(12) United States Patent
Yeudall et al.

(10) Patent No.: US 12,115,087 B2
(45) Date of Patent: Oct. 15, 2024

(54) SENSOR FOR PROSTHETIC CONTROL

(71) Applicant: Touch Bionics Limited, Livingston (GB)

(72) Inventors: Abram David Yeudall, Inverkip (GB); John Andrew McDaid, Skelmorlie (GB); Steven Byrne, Edinburgh (GB); Hugh Gill, Strathclyde (GB); Rodrigo Mercader Rivera, Livingston (GB)

(73) Assignee: Touch Bionics Limited, Livingston (GB)

( * ) Notice: Subject to any disclaimer, the term of this patent is extended or adjusted under 35 U.S.C. 154(b) by 238 days.

(21) Appl. No.: 17/517,576

(22) Filed: Nov. 2, 2021

(65) Prior Publication Data
US 2022/0133510 A1 May 5, 2022

Related U.S. Application Data

(60) Provisional application No. 63/109,151, filed on Nov. 3, 2020.

(51) Int. Cl.
*A61F 2/72* (2006.01)
*G01D 5/14* (2006.01)
(Continued)

(52) U.S. Cl.
CPC ............... *A61F 2/72* (2013.01); *G01D 5/145* (2013.01); *A61F 2/583* (2013.01); *A61F 2/68* (2013.01); *A61F 2/70* (2013.01); *A61F 2002/764* (2013.01)

(58) Field of Classification Search
CPC ...... A61F 2/72; A61F 2/68; A61F 2/70; A61F 2002/764; A61F 2/54; A61F 2/60; G01D 5/145
See application file for complete search history.

(56) References Cited

U.S. PATENT DOCUMENTS

| 2,669,727 A | 2/1954 | Opuszenski |
| 3,822,418 A | 7/1974 | Popov et al. |
(Continued)

FOREIGN PATENT DOCUMENTS

| CN | 1803413 | 7/2006 |
| CN | 111067677 | 4/2020 |
(Continued)

OTHER PUBLICATIONS

International Preliminary Report on Patentability and Written Opinion in Application No. PCT/GB2010/051529, mailed Apr. 5, 2012.
(Continued)

*Primary Examiner* — Bruce E Snow
(74) *Attorney, Agent, or Firm* — Knobbe, Martens, Olson & Bear, LLP

(57) ABSTRACT

A sensor assembly for a prosthetic or orthotic device (POD) may include a housing and a support. The housing may be attached with the POD. The support may be moveably connected with the housing such that the support may move relative to the housing. The support may form an enclosure with the housing. Within the enclosure, the sensor assembly may include one or more sensors and a circuit board. The one or more sensors may include one or more of an inertial measurement unit, an electromyography sensor, or a distance sensor such as a magnetic sensor and a magnet. The circuit board may be attached with the support and in electrical communication with the plurality of sensors. Movement of the support may cause the sensors to move which may be detected for control of the POD. The sensor assembly may be attached to an arm or other prosthetic socket for detection of natural limb movements.

21 Claims, 30 Drawing Sheets

(51) Int. Cl.
  *A61F 2/58* (2006.01)
  *A61F 2/68* (2006.01)
  *A61F 2/70* (2006.01)
  *A61F 2/76* (2006.01)

(56) References Cited

U.S. PATENT DOCUMENTS

| | | |
|---|---|---|
| 3,866,246 A | 2/1975 | Seamone et al. |
| 4,030,141 A | 6/1977 | Graupe |
| 4,213,467 A | 7/1980 | Stulen et al. |
| 4,409,529 A | 10/1983 | Basford et al. |
| 4,558,704 A | 12/1985 | Petrofsky |
| 4,623,354 A | 11/1986 | Childress et al. |
| 4,808,187 A | 2/1989 | Patterson et al. |
| 4,955,918 A | 9/1990 | Lee |
| 4,990,162 A | 2/1991 | LeBlanc et al. |
| 5,246,463 A | 9/1993 | Giampapa |
| 5,413,611 A * | 5/1995 | Haslam, II ............ A61F 2/583 623/24 |
| 5,888,213 A | 3/1999 | Sears et al. |
| 5,888,246 A | 3/1999 | Gow |
| 6,244,873 B1 | 6/2001 | Hill et al. |
| 6,344,062 B1 | 2/2002 | Abboudi et al. |
| 6,494,662 B1 | 12/2002 | De Montalembert |
| 6,589,287 B2 | 7/2003 | Lundborg |
| 6,660,042 B1 | 12/2003 | Curcie et al. |
| 6,684,754 B2 | 2/2004 | Comer |
| 7,056,297 B2 | 6/2006 | Dohno et al. |
| 7,370,896 B2 | 5/2008 | Anderson et al. |
| 7,373,721 B2 | 5/2008 | Bergamasco et al. |
| 7,828,857 B2 | 11/2010 | Farnsworth et al. |
| 7,922,773 B1 | 4/2011 | Kuiken |
| 8,197,554 B2 | 6/2012 | Whiteley et al. |
| 8,396,546 B2 | 3/2013 | Hirata et al. |
| 8,593,255 B2 | 11/2013 | Pang et al. |
| 8,662,552 B2 | 3/2014 | Torres-Jara |
| 8,696,763 B2 | 4/2014 | Gill |
| 8,808,397 B2 | 8/2014 | Gow |
| 8,821,587 B2 | 9/2014 | Lanier et al. |
| 8,840,680 B2 | 9/2014 | Goldfarb et al. |
| 9,034,055 B2 | 5/2015 | Vinjamuri et al. |
| 9,072,616 B2 | 7/2015 | Schulz |
| 9,114,030 B2 | 8/2015 | van der Merwe et al. |
| 9,121,699 B2 | 9/2015 | van der Merwe et al. |
| 9,174,339 B2 | 11/2015 | Goldfarb et al. |
| 9,265,625 B2 | 2/2016 | Goldfarb et al. |
| 9,278,012 B2 | 3/2016 | Gill |
| 9,402,749 B2 | 8/2016 | Gill et al. |
| 9,463,100 B2 | 10/2016 | Gill |
| 9,720,515 B2 | 8/2017 | Wagner et al. |
| 9,730,815 B2 | 8/2017 | Goldfarb et al. |
| 9,826,933 B2 | 11/2017 | van der Merwe et al. |
| 9,901,465 B2 | 2/2018 | Lanier, Jr. et al. |
| 9,931,230 B2 | 4/2018 | Sikdar et al. |
| 10,047,908 B1 | 8/2018 | Bohle et al. |
| 10,265,197 B2 | 4/2019 | Gill et al. |
| 10,318,863 B2 | 8/2019 | Lock et al. |
| 10,369,024 B2 | 8/2019 | Gill |
| 10,398,576 B2 | 9/2019 | Gill et al. |
| 10,610,385 B2 | 4/2020 | Meijer et al. |
| 11,185,426 B2 | 11/2021 | Gill et al. |
| 11,234,842 B2 | 2/2022 | Gill et al. |
| 11,259,941 B2 | 3/2022 | Gill et al. |
| 11,547,581 B2 | 1/2023 | Byrne et al. |
| 11,890,208 B2 | 2/2024 | Meijer et al. |
| 2003/0036805 A1 | 2/2003 | Senior |
| 2003/0191454 A1 | 10/2003 | Niemeyer |
| 2004/0103740 A1 | 6/2004 | Townsend et al. |
| 2005/0192677 A1 | 9/2005 | Ragnarsdottir et al. |
| 2006/0158146 A1 | 7/2006 | Tadano |
| 2006/0167564 A1 | 7/2006 | Flaherty et al. |
| 2006/0212129 A1 | 9/2006 | Lake et al. |
| 2008/0058668 A1 | 3/2008 | Seyed Momen et al. |
| 2008/0146981 A1 | 6/2008 | Greenwald et al. |
| 2008/0215162 A1 | 9/2008 | Farnsworth et al. |
| 2008/0262634 A1 | 10/2008 | Puchhammer |
| 2009/0030530 A1 | 1/2009 | Martin |
| 2009/0302626 A1 | 12/2009 | Dollar et al. |
| 2010/0016990 A1 | 1/2010 | Kurtz |
| 2010/0036507 A1 | 2/2010 | Gow |
| 2010/0116078 A1 | 5/2010 | Kim |
| 2010/0274365 A1 | 10/2010 | Evans et al. |
| 2010/0328049 A1 | 12/2010 | Frysz et al. |
| 2011/0136376 A1 | 6/2011 | Johnson et al. |
| 2011/0257765 A1 | 10/2011 | Evans et al. |
| 2011/0264238 A1 | 10/2011 | van der Merwe et al. |
| 2012/0061155 A1 | 3/2012 | Berger et al. |
| 2012/0123558 A1 | 5/2012 | Gill |
| 2012/0221122 A1 | 8/2012 | Gill et al. |
| 2012/0280812 A1 | 11/2012 | Sheikman et al. |
| 2012/0286629 A1 | 11/2012 | Johnson et al. |
| 2012/0330439 A1 | 12/2012 | Goldfarb et al. |
| 2013/0030550 A1 * | 1/2013 | Jopek ............ A61F 2/588 623/64 |
| 2013/0053984 A1 | 2/2013 | Hunter et al. |
| 2013/0059467 A1 | 3/2013 | Johnson et al. |
| 2013/0253705 A1 | 9/2013 | Goldfarb et al. |
| 2013/0317648 A1 | 11/2013 | Assad |
| 2014/0324189 A1 * | 10/2014 | Gill ............ B25J 15/0009 623/24 |
| 2014/0371871 A1 | 12/2014 | Farina et al. |
| 2015/0142082 A1 | 5/2015 | Simon et al. |
| 2015/0216681 A1 | 8/2015 | Lipsey et al. |
| 2015/0328019 A1 | 11/2015 | Park et al. |
| 2015/0351935 A1 | 12/2015 | Donati et al. |
| 2015/0374515 A1 | 12/2015 | Meijer et al. |
| 2016/0120664 A1 | 5/2016 | Schultz |
| 2016/0143751 A1 | 5/2016 | Chestek et al. |
| 2016/0166409 A1 | 6/2016 | Goldfarb et al. |
| 2016/0287422 A1 | 10/2016 | Kelly et al. |
| 2017/0049583 A1 | 2/2017 | Belter et al. |
| 2017/0049586 A1 | 2/2017 | Gill et al. |
| 2017/0203432 A1 | 7/2017 | Andrianesis |
| 2017/0209288 A1 | 7/2017 | Veatch |
| 2017/0340459 A1 | 11/2017 | Mandelbaum |
| 2018/0014744 A1 | 1/2018 | Duerstock et al. |
| 2018/0020973 A1 | 1/2018 | Hurley et al. |
| 2018/0098865 A1 | 4/2018 | Mojica et al. |
| 2018/0116829 A1 | 5/2018 | Gaston et al. |
| 2018/0168477 A1 | 6/2018 | Graimann et al. |
| 2018/0192909 A1 | 7/2018 | Einarsson et al. |
| 2018/0221177 A1 | 8/2018 | Kaltenbach et al. |
| 2018/0235782 A1 | 8/2018 | Choi et al. |
| 2018/0256365 A1 | 9/2018 | Bai |
| 2019/0000380 A1 | 1/2019 | Moradi et al. |
| 2019/0216618 A1 | 7/2019 | Gill |
| 2019/0298551 A1 | 10/2019 | Gibbard et al. |
| 2019/0307584 A1 | 10/2019 | Huang et al. |
| 2019/0375067 A1 | 12/2019 | Berrocal et al. |
| 2020/0054466 A1 | 2/2020 | Gill et al. |
| 2020/0060847 A1 | 2/2020 | Ferguson et al. |
| 2020/0197193 A1 | 6/2020 | Byrne et al. |
| 2020/0268532 A1 | 8/2020 | Meijer et al. |
| 2021/0137706 A1 | 5/2021 | LaChappelle |
| 2022/0151805 A1 | 5/2022 | Gill et al. |
| 2023/0022882 A1 | 1/2023 | Byrne et al. |
| 2023/0096427 A1 | 3/2023 | Byrne et al. |
| 2023/0338170 A1 | 10/2023 | Norberg |
| 2023/0338171 A1 | 10/2023 | Norberg et al. |

FOREIGN PATENT DOCUMENTS

| | | |
|---|---|---|
| EP | 0 145 504 | 6/1985 |
| EP | 1 043 003 | 10/2000 |
| EP | 2 114 316 | 7/2014 |
| EP | 2 125 091 | 4/2016 |
| EP | 2 467 101 | 4/2016 |
| EP | 2 696 814 | 1/2017 |
| GB | 1 585 256 | 2/1981 |
| GB | 2 278 281 | 11/1994 |
| GB | 2 302 949 | 5/1997 |
| GB | 2 444 679 | 6/2008 |
| JP | 53-011456 | 2/1978 |
| JP | 2001-082913 | 3/2001 |

(56) References Cited

FOREIGN PATENT DOCUMENTS

| WO | WO 95/024875 | 9/1995 |
|---|---|---|
| WO | WO 00/069375 | 11/2000 |
| WO | WO 02/049534 | 6/2002 |
| WO | WO 03/017878 | 3/2003 |
| WO | WO 03/017880 | 3/2003 |
| WO | WO 2006/069264 | 6/2006 |
| WO | WO 2006/078432 | 7/2006 |
| WO | WO 2006/086504 | 8/2006 |
| WO | WO 2007/063266 | 6/2007 |
| WO | WO 2007/076764 | 7/2007 |
| WO | WO 2007/076765 | 7/2007 |
| WO | WO 2007/126854 | 11/2007 |
| WO | WO 2007/127973 | 11/2007 |
| WO | WO 2008/044207 | 4/2008 |
| WO | WO 2008/098059 | 8/2008 |
| WO | WO 2008/098072 | 8/2008 |
| WO | WO 2010/018358 | 2/2010 |
| WO | WO 2010/149967 | 12/2010 |
| WO | WO 2011/001136 | 1/2011 |
| WO | WO 2011/022569 | 2/2011 |
| WO | WO 2011/036473 | 3/2011 |
| WO | WO 2011/036626 | 3/2011 |
| WO | WO 2011/107778 | 9/2011 |
| WO | WO 2012/071343 | 5/2012 |
| WO | WO 2014/111843 | 7/2014 |
| WO | WO 2014/122455 | 8/2014 |
| WO | WO 2017/137930 | 8/2017 |
| WO | WO 2018/054945 | 3/2018 |
| WO | WO 2018/132711 | 7/2018 |
| WO | WO 2018/178420 | 10/2018 |
| WO | WO 2018/218129 | 11/2018 |
| WO | WO 2018/236208 | 12/2018 |
| WO | WO 2020/113082 | 6/2020 |
| WO | WO 2021/124060 | 6/2021 |

OTHER PUBLICATIONS

International Search Report and Written Opinion in Application No. PCT/IB2021/060147, mailed Mar. 22, 2022.
Antonio et al., "A Virtual Upper Limb Prosthesis as a Training System", 7th International Conference on Electrical Engineering, Computing Science and Automatic Control (CCE 2010) Tuxtla Gutiérrez, Chiapas, México. Sep. 8-10, 2010, pp. 210-215.
Baek et al., "Design and Control of a Robotic Finger for Prosthetic Hands", Proceedings of the 1999 IEEE International Conference on Intelligent Robots and Systems, pp. 113-117.
Butterfab et al., "DLR-Hand II: Next Generation of a Dextrous Robot Hand", IEEE International Conference on Robotics and Automation, Seoul, Korea, May 21-26, 2001, vol. 1, pp. 109-114.
Connolly, "Prosthetic Hands from Touch Bionics", Industrial Robot, Emerald Group Publishing Limited, Jun. 2008, vol. 35, No. 4, pp. 290-293.
Cotton et al., "Control Strategies for a Multiple Degree of Freedom Prosthetic Hand", Measurement + Control, Feb. 2007, vol. 40, No. 1, pp. 24-27.
"DC Circuit Theory", https://www.electronics-tutorials.ws/dccircuits/dcp_1.html, Date verified by the Wayback Machine Apr. 23, 2013, pp. 16.
Dellorto, Danielle, "Bionic Hands Controlled by iPhone App", CNN, Apr. 12, 2013, pp. 4 http://www.cnn.com/2013/04/12/health/bionic-hands.
"dsPIC Microcontrollers Introduction and Features", https://microcontrollerslab.com/dspic-microcontrollers-introduction/, Aug. 1, 2017, pp. 4.
"DuPont Engineering Design—The Review of DuPont Engineering Polymers in Action", http://www.engpolymer.co.kr/x_data/magazine/engdesign07_2e.pdf, Feb. 2007, pp. 16.
Edsinger-Gonzales, Aaron, "Design of a Compliant and Force Sensing Hand for a Humanoid Robot", 2005, pp. 5.
Fildes, Jonathan, "Bionic Hand Wins Top Tech Prize", BBC News, Jun. 9, 2008, http://news.bbc.co.uk/2/hi/science/nature/7443866.stm, pp. 3.

Fukuda et al., "Training of Grasping Motion Using a Virtual Prosthetic Control System", 2010 IEEE International Conference on Systems Man and Cybernetics (SMC), Oct. 10-13, 2010, pp. 1793-1798.
Gaiser et al., "A New Anthropomorphic Robotic Hand", 2008 8th IEEE-RAS International Conference on Humanoid Robots, Dec. 1-3, 2008, Daejeon, Korea, pp. 418-422.
Grip Chips™, Datasheet, May 15, 2014, Issue 1, http://touchbionics.com/sites/default/files/files/Grip%20Chip%20datasheet%20May%202014.pdf, pp. 1.
"iLimb Bionic Hand Now Ready for Market", Technovelgy.com, www.technovelgy.com/ct/Science-Fiction-News.asp?NewsNum=1125, as printed Jul. 6, 2020 in 3 pages.
Kargov et al., "Applications of a Fluidic Artificial Hand in the Field of Rehabilitation", Rehabilitation Robotics, Ch. 15, Aug. 2007, pp. 261-286.
Kargov et al., "Development of a Multifunctional Cosmetic Prosthetic Hand", Proceedings for the 2007 IEEE 10th International Conference on Rehabilitation Robotics, Jun. 12-15, 2007, Noordwijk, The Netherlands, pp. 550-553.
Kargov et al., "Modularly Designed Lightweight Anthropomorphic Robot Hand", 2006 IEEE International Conference on Multisensor Fusion and Integration for Intelligent Systems, Sep. 3-6, 2006, Heidelberg, Germany, pp. 155-159.
Kawasaki et al., "Design and Control of Five-Fingered Haptic Interface Opposite to Human Hand", IEEE Transactions on Robotics, Oct. 2007, vol. 23, No. 5., pp. 909-918.
Kim et al., "Development of Anthropomorphic Prosthesis Hand $H^3$ and Its Control", 4th WSEAS/IASME International Conference on Dynamical Systems and Control (Control'08) Corfu, Greece, Oct. 26-28, 2008, pp. 133-138.
Kyberd et al., "Two-Degree-of-Freedom Powered Prosthetic Wrist", Journal of Rehabilitation Research & Development, Jul. 2011, vol. 48, No. 6, pp. 609-617.
Lamounier et al., "On the Use of Virtual and Augmented Reality for Upper Limb Prostheses Training and Simulation", 2010 Annual International Conference of the IEEE Engineering in Medicine and Biology Society (EMBC), Aug. 31-Sep. 4, 2010, pp. 2451-2454.
Lotti et al., "UBH 3: A Biologically Inspired Robotic Hand", Jan. 2004, pp. 7.
Mace et al., "Augmenting Neuroprosthetic Hand Control Through Evaluation of a Bioacoustic Interface", IEEE/RSJ International Conference on Intelligent Robots and Systems (IROS), Tokyo, Japan, Nov. 3-7, 2013, pp. 7.
Martinez-Villalpando et al., "Agonist-Antagonist Active Knee Prosthesis: A Preliminary Study in Level-Ground Walking", Journal of Rehabilitation Research & Development, vol. 46, No. 3, 2009, pp. 361-374.
MEC '05: Integrating Prosthetics and Medicine, University of New Brunswick's MyoElectric Controls/Powered Prosthetics Symposium, Aug. 17-19, 2005, Fredericton NB Canada, pp. 260.
Osborn et al., "Utilizing Tactile Feedback for Biomimetic Grasping Control in Upper Limb Prostheses", Department of Biomedical Engineering, Johns Hopkins University, Baltimore, USA, Nov. 5, 2013, pp. 4.
Pedrocchi et al., "MUNDUS Project: Multimodal Neuroprosthesis for Daily Upper Limb Support", Journal of Neuroengineering and Rehabilitation, Jul. 2013, vol. 10, No. 66, pp. 20.
Poppe, Zytel HTN Provides a Helping Hand, DuPont Engineering Design 8 (2007), pp. 3.
Press Release, "Touch Bionics Introduce Digitally Controlled Supro Wrist", http://www.touchbionics.com/news-events/news/touch-bionics-introduce-digitally-controlled-supro-wrist, May 3, 2016 in 2 pages.
Puig et al., "A Methodology for the Design of Robotic Hands with Multiple Fingers", International Journal of Advanced Robotic Systems, 2008, vol. 5, No. 2, pp. 177-184.
Pylatiuk et al., "Design and Evaluation of a Low-Cost Force Feedback System for Myoelectric Prosthetic Hands", 18 J. Prosthetics and Orthotics 57-61 (2006).
Pylatiuk et al., "Results of an Internet Survey of Myoelectric Prosthetic Hand Users", Prosthetics and Orthotics International, Dec. 2007, vol. 31, No. 4, pp. 362-370.

(56) References Cited

OTHER PUBLICATIONS

Ryew et al., "Robotic Finger Mechanism with New Anthropomorphic Metacarpal Joint", 26th Annual Conference of the IEEE Industrial Electronics Society, 2000. IECON 2000, vol. 1, pp. 416-421.
Schulz et al., "Die Entwicklung Einer Multifunktionalen Kosmetischen Handprothese", Prothetik, Orthopädie-Technik, Aug. 2006, pp. 627-632.
Stix, Gary, "Phantom Touch: Imbuing a Prosthesis with Manual Dexterity", Scientific American, Oct. 1998, pp. 41 & 44.
"Supro Wrist", Touch Bionics, https://web.archive.org/web/20160928141440/http://www.touchbionics.com/products/supro-wrist as archived Sep. 28, 2016 in 3 pages.
The Weir Thesis ("Weir Thesis") is entitled "An Externally-Powered, Myo-Electrically Controlled Synergetic Prosthetic Hand for the Partial-Hand Amputee", published Aug. 1989, pp. 365. (Uploaded in 3 Parts).
"Touch Bionics Grip Chips Let Hand Prostheses Think for Themselves", May 15, 2014, www.medgadget.com/2014/05/touch-bionics-grip-chips-let-hand-prostheses-think-for-themselves.html, . 2.
Touch Bionics PowerPoint Presentation in 3 pages, believed to be shown at ISPO Conference in Leipzig, Germany, May 2016. (Applicant requests that the Examiner consider this reference as qualifying as prior art as of the date indicated, but Applicant does not admit its status as prior art by submitting it here and reserves the right to challenge the reference's prior art status at a later date).
Touch Bionics PowerPoint Slide in 1 page, believed to be presented at Advanced Arm Dynamics company Jan. 11, 2016. (Applicant requests that the Examiner consider this reference as qualifying as prior art as of the date indicated, but Applicant does not admit its status as prior art by submitting it here and reserves the right to challenge the reference's prior art status at a later date).
Touch Bionics Screenshots of video in PowerPoint Presentation in 4 pages, believed to be shown at ISPO Conference in Leipzig, Germany, May 2016. (Applicant requests that the Examiner consider this reference as qualifying as prior art as of the date indicated, but Applicant does not admit its status as prior art by submitting it here and reserves the right to challenge the reference's prior art status at a later date).
Trachtenberg et al., "Radio Frequency Identification, An Innovative Solution to Guide Dexterous Prosthetic Hands", 33rd Annual International Conference of the IEEE Embs, Boston, MA, Aug. 30-Sep. 3, 2011, pp. 4.
Vilarino, Martin, "A Novel Wireless Controller for Switching among Modes for an Upper-Limb Prosthesis", The Academy Today, Jan. 2014, vol. 10, No. 1, pp. A-12 to A-15.
Ward, Derek Kempton, "Design of a Two Degree of Freedom Robotic Finger", Sep. 1996, in 155 pages.
Weir et al., "A Myoelectrically Controlled Prosthetic Hand for Transmetacarpal Amputations", JPO Journal of Prosthetics and Orthotics, Jun. 2001, vol. 13, No. 2, pp. 26-31.
Weir et al., "The Design and Development of a Synergetic Partial Hand Prosthesis with Powered Fingers", RESNA '89, Proceedings of the 12th Annual Conference, Technology for the Next Decade, Jun. 25-30, 1989, pp. 473-474.
"World's First Bionic Hand Factory Opened by Scottish Company", DailyMail.com, Jan. 8, 2008, https://www.dailymail.co.uk/sciencetech/article-506661/Worlds-bionic-hand-factory-opened-Scottish-company.html, pp. 4.
International Search Report and Written Opinion in Application No. PCT/GB2010/001232, mailed Oct. 6, 2010.
International Preliminary Report on Patentability and Written Opinion in Application No. PCT/GB2010/001232, mailed Jan. 4, 2012.
International Search Report and Written Opinion in Application No. PCT/GB2012/052111, mailed Nov. 26, 2012.
International Preliminary Report on Patentability and Written Opinion in Application No. PCT/GB2012/052111, mailed Mar. 27, 2014.
International Search Report and Written Opinion in Application No. PCT/GB2012/052021, mailed Nov. 26, 2012.
International Preliminary Report on Patentability and Written Opinion in Application No. PCT/GB2012/052021, mailed Feb. 27, 2014.
International Search Report and Written Opinion in Application No. PCT/GB2012/052263, mailed Dec. 20, 2012.
International Preliminary Report on Patentability and Written Opinion in Application No. PCT/GB2012/052263, mailed Mar. 27, 2014.
International Search Report and Written Opinion in Application No. PCT/GB2010/051529, mailed Jan. 4, 2011.
International Preliminary Report on Patentability and Written Opinion in Application No. PCT/GB2010/051529, mailed Jan. 4, 2011.
International Search Report and Written Opinion in Application No. PCT/GB2014/050331, mailed May 8, 2014.
International Preliminary Report on Patentability and Written Opinion in Application No. PCT/GB2014/050331, mailed Aug. 20, 2015.
International Search Report and Written Opinion in Application No. PCT/GB2015/051356, mailed Jul. 14, 2015.
International Preliminary Report on Patentability and Written Opinion in Application No. PCT/GB2015/051356, mailed Nov. 15, 2016.
International Search Report and Written Opinion in Application No. PCT/IB2016/001713, mailed Jul. 12, 2017.
International Preliminary Report on Patentability and Written Opinion in Application No. PCT/IB2016/001713, mailed Mar. 5, 2019.
International Search Report and Written Opinion in Application No. PCT/IB2019/061146, mailed Apr. 15, 2020.
International Search Report and Written Opinion in Application No. PCT/IB2020/061859, mailed Mar. 16, 2021.

* cited by examiner

| User Movement | Sensor Data - Muscle Contraction | Sensor Data - Forearm Rotation | Classification |
|---|---|---|---|
| | --- EMG ···· Hall-Effect --- Accelerometer | | Hand Open |
| | --- EMG ···· Hall-Effect --- Accelerometer | | Hand Close |
| | --- EMG ···· Hall-Effect --- Accelerometer | | Wrist Supination |
| | --- EMG ···· Hall-Effect --- Accelerometer | | Wrist Pronation |

FIG. 7

SENSOR FOR PROSTHETIC CONTROL

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57. The present application claims priority to U.S. Provisional Patent Application No. 63/109,151, titled "SENSOR FOR PROSTHETIC CONTROL" and filed on Nov. 3, 2020, which is incorporated herein by reference in its entirety for all purposes and forms a part of this specification.

FIELD

The present disclosure relates to prosthetics. More specifically, this disclosure relates to a sensor assembly for prosthetic systems.

BACKGROUND

Amputees benefit greatly from prosthetic replacements for lost limbs. For instance, prosthetic hands, wrists, feet, legs, or arms restore lost functionality and provide independence to users. However, control of a prosthetic device suffers from lack of reliable user data. Improved prosthetic solutions for detecting user inputs for control of prosthetics are therefore desirable.

SUMMARY

The embodiments disclosed herein each have several aspects no single one of which is solely responsible for the disclosure's desirable attributes. Without limiting the scope of this disclosure, its more prominent features will now be briefly discussed. After considering this discussion, and particularly after reading the section entitled "Detailed Description," one will understand how the features of the embodiments described herein provide advantages over existing systems, devices and methods for prosthetic control.

The following disclosure describes non-limiting examples of some embodiments. For instance, other embodiments of the disclosed systems and methods may or may not include the features described herein. Moreover, disclosed advantages and benefits may apply only to certain embodiments of the invention and should not be used to limit the disclosure.

The prosthetic systems and methods described herein are described with respect to upper limb prosthetics but may be used with lower limb prosthetics as well. Prosthetic hand and wrist systems and methods described herein provide a more responsive upper limb prosthetic system for amputees. A prosthetic hand or wrist system may include one or multiple sensor assemblies configured to be placed at one or more locations on a natural limb to capture activity from the user. Each sensor assembly may include one or multiple sensors that obtain a variety of different input signal types from the patient, and a controller that may receive, analyse, and translate the input signals into a movement of the prosthetic device, such as an arm rotation, a wrist rotation, and/or a hand/digit movement. The use of multiple sensors within a single sensor assembly and within a small, nonintrusive package to obtain multiple input signals may substantially increase the opportunity of obtaining useful patient input. For example, the controller may apply any of various arbitration techniques to select, combine, or ignore input signals when translating the input signals into the prosthetic movement. One or more of the one or more sensors may be moveably held by the assembly such that the sensor(s) adjust their position and/or orientation in response to movement of the user's muscle, for example to maintain a particular position and/or orientation relative to the user's muscle.

The present disclosure provides an improved sensor assembly which increases reliability of translating patient input into intended prosthetic movement by allowing for more input data and thus the ability for better classification and accuracy of translation into prosthetic movements. In one aspect, a sensor assembly according to the present disclosure may include a housing and a support. The housing may define a central axis and may be configured to attach with a fitting or a prosthetic or orthotic device (POD). The support may be moveably connected with the housing such that the support is configured to move relative to the housing along the central axis. The support may form an enclosure with the housing. The sensor assembly may further include one or more of a plurality of sensors disposed within the enclosure formed by the support and the housing. The plurality of sensors may include one or more sensors that respond to muscle activation, such as a sensor that is sensitive to force, distance/displacement, potential difference (e.g., voltage), vibrations (for example, of muscle fibers), sound/acoustic readings, or another symptom of muscle activity. The plurality of sensors may include an inertial measurement unit (IMU), an electromyography (EMG) sensor, a microphone, a voltage sensor, a displacement or distance sensor, a force sensitive resistor reading force caused by the displacement of muscle tissue, and/or a magnetic sensor. The sensor assembly may further include a circuit board attached with the support and in electrical communication with the one or more of the plurality of sensors.

Various embodiments of the various aspects described herein may be implemented. For example, the sensor assembly may also include any combination of the following features, among others described herein. An EMG sensor may include multiple EMG pickups carried by the support and configured to contact skin of a user of the POD and to move along with the support. The sensor assembly may further include a magnet. The magnet may be configured to generate a magnetic field that may be detected by a magnetic sensor. The magnet may be attached with the housing and the magnetic sensor may be attached with the support and configured to move along with the support. The sensor assembly may include at least one biasing member configured to bias the support in a direction away from the housing and toward the user. The at least one biasing member may include a compression spring. The IMU may be configured to detect a vibromyography (VMG) signal associated with a muscle of the user. The IMU may include one or more of an accelerometer, a gyroscope, or a magnetometer. The gyroscope may be used to determined limb axial rotation. The magnetic sensor may include one or more of a Hall effect sensor, a magnetometer, or the like.

The sensor assembly may also include any combination of the following features, among others described herein. The sensor assembly may include a tray attached to the support between the support and the housing. The sensor assembly may include a pivot axis perpendicular to the central axis and a sliding axis perpendicular to both the central and pivot axes. The support may be pivotably or slidably connected to the housing such that the support may pivot about the pivot axis relative to the housing or may slide along the sliding axis.

In another aspect, a sensor assembly according to the present disclosure may include a housing and a support. The housing may define a central axis, a pivot axis perpendicular to the central axis, and a sliding axis perpendicular to both the central axis and pivot axis. The housing may be configured to be attached with a fitting or a POD. The support may be moveably connected with the housing such that the support may move relative to the housing. The support may form an enclosure with the housing. The support may be pivotably or slidably connected to the housing such that the support may pivot about the pivot axis or may slide along the sliding axis. The sensor assembly may include one or more of a plurality of sensors disposed within the enclosure. The plurality of sensors may be configured to detect indications of muscle activity. For example, the plurality of sensors may be configured to detect one or more of electrical signals associated with a residual limb or a sound limb of a user of the POD, translation of a muscle of the residual limb or the sound limb of the user, inertial forces generated by movement of the residual limb or the sound limb of the user, force, distance/displacement, potential difference, or vibrations. The sensor assembly may include a circuit board disposed within the enclosure and in electrical communication with the one or more of the plurality of sensors.

The sensor assembly may also include any combination of the following features, among others described herein. The plurality of sensors may include an inertial measurement unit (IMU). The IMU may include at least one of an accelerometer, a gyroscope, and/or a magnetometer. The plurality of sensors may include an electromyography (EMG) sensor. The EMG sensor may include multiple EMG pickups carried by the support and configured to contact the residual limb or the sound limb of the user. The plurality of sensors may include a magnetic sensor. The sensor assembly may further include a magnet. The magnet may be configured to generate a magnetic field that may be detected by the magnetic sensor. The plurality of sensors may include a displacement sensor, a distance sensor, a microphone, or a voltage sensor. The sensor assembly may include at least one biasing member configured to bias the support along the sliding axis in a direction away from the housing and toward the user. The at least one biasing member may include a compression spring.

The present disclosure provides an improved apparatus for restoring mobility to an amputee with various advantages. For example, the apparatus may increase reliability of translating patient input into intended prosthetic movement by allowing for more input data and thus the ability for better classification and accuracy of translation into prosthetic movements. An apparatus for restoring mobility to an amputee may include a prosthetic or orthotic device (POD) and a fitting. The fitting may be configured to attach to the POD and to a residual limb or a sound limb of a user of the POD. The apparatus may further include a sensor assembly configured to attach with the fitting and configured to contact the residual limb or the sound limb when the fitting is attached to the residual limb or the sound limb. The sensor assembly may include an enclosure formed by a housing and a support. The support may be moveably connected with the housing. The sensor assembly may include one or more of a plurality of sensors carried by the enclosure. The plurality of sensors may include an inertial measurement unit (IMU), an electromyography (EMG) sensor, a magnetic sensor, a microphone, or a voltage sensor. The sensor assembly may include a circuit board in electrical communication with the one or more of the plurality of sensors.

The apparatus and embodiments thereof of any of the preceding paragraphs may also include any combination of the following features described in this paragraph, among others described herein. The support may include a tray. The support may include one or more EMG pickups of the EMG sensor. The support may be pivotably connected to the housing such that the support may pivot relative to the housing. The support may be slidably connected to the housing such that the support may slide relative to the housing. The IMU may include at least one of an accelerometer, a gyroscope, or a magnetometer. The EMG sensor may include multiple EMG pickups carried by the support and configured to contact the residual limb or the sound limb of the user. The apparatus may further include a magnet. The apparatus may further include a grommet configured to attach to the fitting. The sensor assembly can attach to the fitting via the grommet.

The apparatus and embodiments thereof of any of the preceding paragraphs may also include any combination of the following features described in this paragraph, among others described herein. The base portion or housing of the sensor assembly can include a cutout and the top portion of the sensor assembly can include a locking device including a detent. The cutout can receive the detent of the locking device and facilitate movement of the top portion relative to the base portion. The top portion of the sensor assembly can include a groove that can receive an O-ring, wherein the O-ring can abut against sidewalls of the base portion and create a seal. The groove can include ridges positioned at corners of the top portion and extend vertically within the groove. The ridges can cause the O-ring to stretch around the corners and push the O-ring outwards. This can allow the O-ring to contact inner surface of sidewalls of the base portion and create a seal.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several embodiments in accordance with the disclosure and are not to be considered limiting of its scope, the disclosure will be described with additional specificity and detail through use of the accompanying drawings. In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the drawing, may be arranged, substituted, combined, and designed in a wide variety of different configurations, all of which are explicitly contemplated and make part of this disclosure.

FIG. 7 is a table illustrating various example associations between input signals and hand gestures or hand grips for generating inputs to the sensor assembly.

DETAILED DESCRIPTION

The following detailed description is directed to certain specific embodiments of the development. In this description, reference is made to the drawings wherein like parts or steps may be designated with like numerals throughout for clarity. Reference in this specification to "one embodiment," "an embodiment," or "in some embodiments" means that a particular feature, structure, or characteristic described in connection with the embodiment is included in at least one embodiment of the invention. The appearances of the phrases "one embodiment," "an embodiment," or "in some embodiments" in various places in the specification are not necessarily all referring to the same embodiment, nor are separate or alternative embodiments necessarily mutually exclusive of other embodiments. Moreover, various features are described which may be exhibited by some embodiments and not by others. Similarly, various requirements are described which may be requirements for some embodiments but may not be requirements for other embodiments.

The prosthetic hand and wrist system and methods described herein provide a more responsive upper limb prosthetic system for amputees. A prosthetic hand or wrist system may include one or multiple sensor assemblies fitted to an internal side of a fitting worn on a stump of an amputee. The sensor assemblies are located at different sites on the fitting such that when the fitting is worn by the user the sensor assemblies are aligned with various forearm flexor or extensor muscles. In this way, the sensor assemblies may capture information regarding muscle activity or movement. Each sensor assembly may include a plurality of sensors. In some cases, the plurality of sensors can be referred to as muscle activity sensors. A sensor assembly may include one or more of an electromyography (EMG) sensor, a magnetic sensor (e.g., a Hall effect sensor, a magnetometer, etc.), a mechanomyography (MMG) sensor, an inertial measurement unit (IMU), an accelerometer, a gyroscope, a sound sensor (e.g., an acoustic sensor, a microphone), etc. A controller may translate signals received from the sensor assemblies (sometimes referred to as input signals) into a prosthetic movement.

In general, the ability of individuals to apply input to a prosthetic device may be wide and varied. This, in combination with sub-optimal sensor positioning on the individual may make the harvesting of useful patient input difficult. The prosthetic hand and wrist system of the present disclosure addresses these and other concerns by utilizing multiple measurement sites and multiple sensors with different data types at each measurement site. In this way, the disclosed system allows individuals to provide input using multiple different inputs, and a controller may use any of various arbitration techniques to select, combine, or ignore input signals when translating the input signals into the prosthetic movement.

Figure 1A:
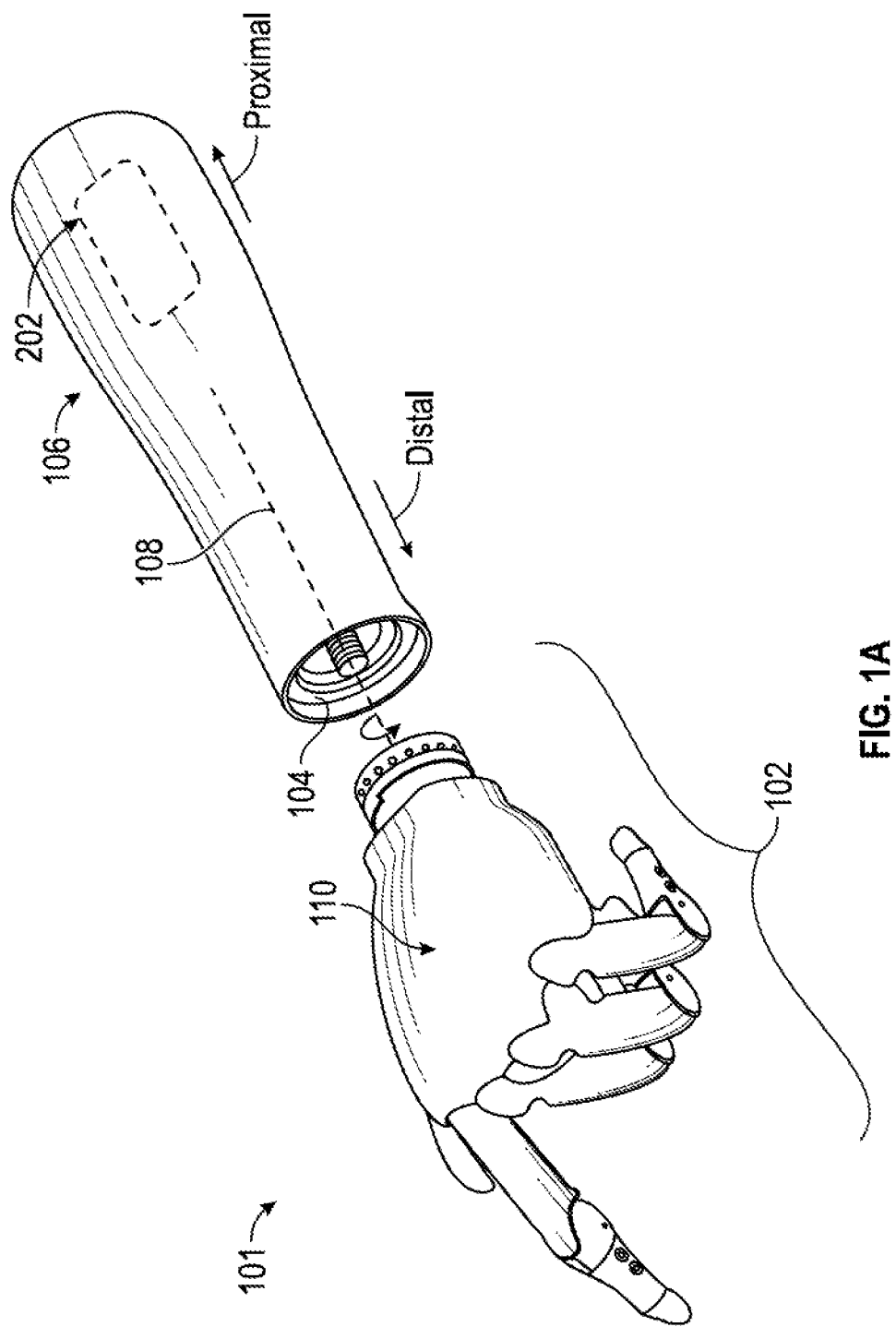
FIG. 1A is a perspective exploded view of an embodiment of a lower arm prosthetic system that may use the sensor assembly described herein.

Furthermore, the present disclosure provides for an improved sensor assembly which increases reliability of translating patient input into intended prosthetic movement by allowing for more input data and thus the ability for better classification and accuracy of translation into prosthetic movements. The sensor assembly of the present disclosure includes multiple sensor types in a single package, thereby providing multiple separate input paths for the individual to act on. This may increase the reliability of a translation from user input to prosthetic movement by allowing multiple dimensions of patient input and thus increasing the opportunity of obtaining useful patient input FIG. 1A is a perspective view of an example lower arm prosthetic system 100, with a prosthetic hand 102 shown as detached from a prosthetic wrist 104. For sake of description, various geometric references are used. A "distal" direction and a "proximal" direction are indicated. As shown, the prosthetic wrist 104 is located proximally relative to the prosthetic hand 102, and the prosthetic hand 102 is located distally relatively to the prosthetic wrist 104. The distal and proximal directions refer to, respectively, directions farther from and closer to a user of the lower arm prosthetic system 100 along the length of an arm of the user containing the lower arm prosthetic system 100. A longitudinal axis 108 is an axis of rotation about which the prosthetic wrist 104 and prosthetic hand 102 rotate. The distal and proximal directions may be directions along the longitudinal axis 108, for example when the lower arm prosthetic system 100 is oriented as shown. "Inner," "inward," and like terms refer to directions toward the longitudinal axis 108, while "outer," "outward," and like terms refer to directions away from the longitudinal axis 108, unless otherwise indicated.

The prosthetic wrist 104 may be attached to the prosthetic hand 102 to cause movement of the prosthetic hand 102 and thereby forming the complete lower arm prosthetic system 100. A rotatable portion of the prosthetic wrist 104 may be coupled with, for example attached to, the prosthetic hand 102. The rotatable portion of the prosthetic wrist 104 rotates, thereby causing rotation of the prosthetic hand 102. The prosthetic wrist 104 and prosthetic hand 102 rotate about the longitudinal axis 108. The prosthetic hand 102 may form a plurality of different grips, for example different palm or digit positions. The lower arm prosthetic system 100 may synchronize the rotation of the prosthetic wrist 104 with the formation of one of the grips with the prosthetic hand 102. These movements may be based on data received and analyzed by a sensor assembly 202, as described herein.

The prosthetic lower arm 106 is a prosthetic for the lower or outer segment of an arm, for example the forearm. The prosthetic lower arm 106 is a hollow tube with an arm-like shape. The prosthetic lower arm 106 may have a variety of other suitable shapes and configurations. The proximal end of the prosthetic lower arm 106 attaches to a user, for example to a stump of an amputee, a fitting, socket, etc. The distal end of the prosthetic lower arm 106 attaches to the prosthetic wrist 104. The prosthetic lower arm 106 may be mechanically or electrically connected to the prosthetic wrist 104. The prosthetic lower arm 106 may include one or more of the sensor assemblies 202 as further described herein, for example attached to an inner surface thereof.

When attached to the prosthetic wrist 104, the prosthetic hand 102 may rotate about the longitudinal axis 108 as indicated, while the prosthetic lower arm 106 remains rotationally stationary. Thus, the prosthetic hand 102, when attached to the prosthetic wrist 104, may rotate about the longitudinal axis 108 relative to the prosthetic lower arm 106. The rotation of the prosthetic hand 102 is caused by the prosthetic wrist 104.

The lower arm prosthetic system 100 described herein is merely an example of a prosthetic lower arm, prosthetic wrist, or prosthetic hand system that may use the sensor assembly 202. Other prosthetic hands, wrists, or arms may be implemented, for example as described in U.S. Pat. No. 10,369,024, titled SYSTEMS AND METHODS FOR PROSTHETIC WRIST ROTATION and issued on Nov. 2, 2016, the entire content of which is incorporated by reference herein for all purposes.

Figure 1B:
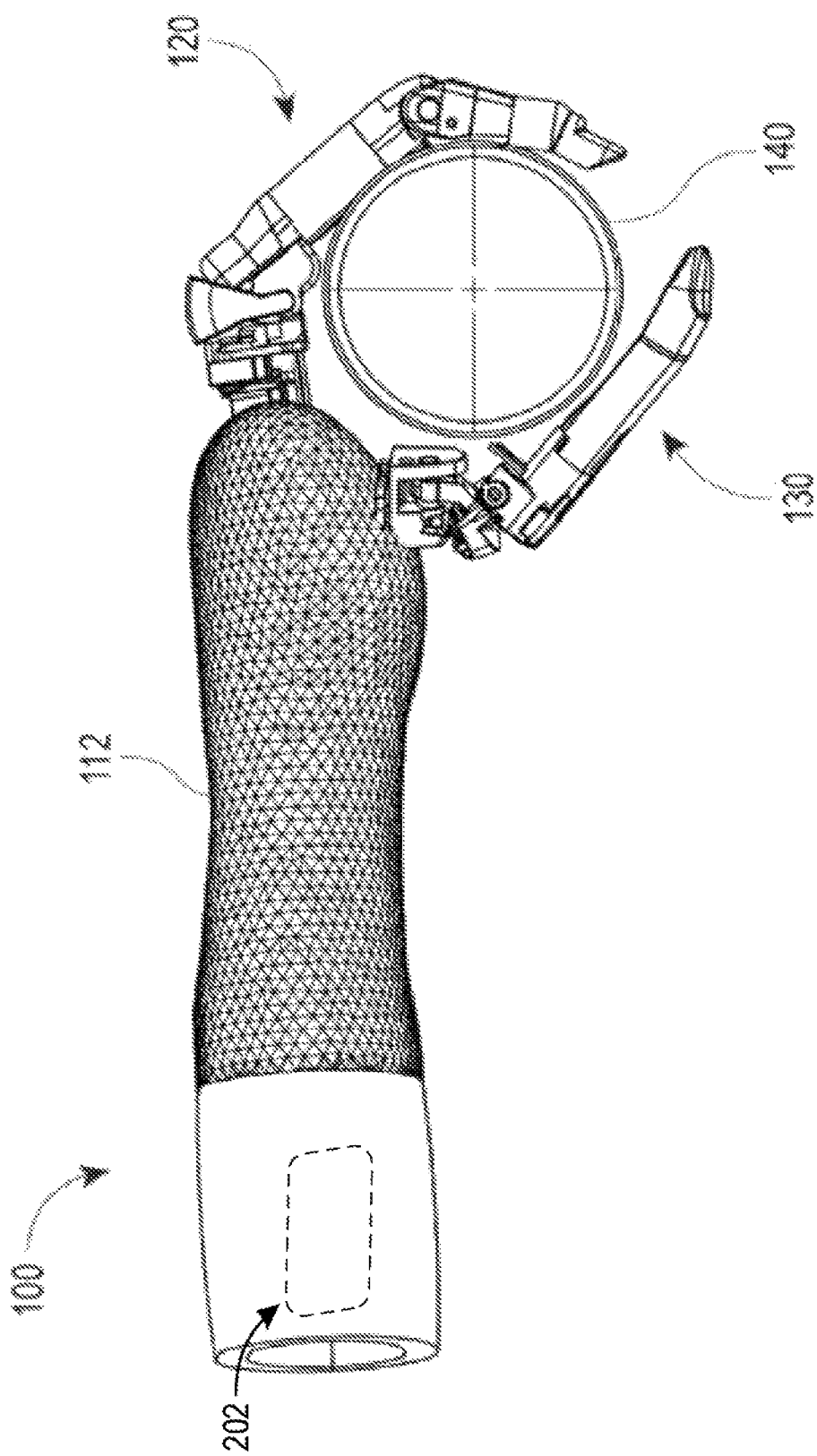
FIG. 1B is a side view of another embodiment of a lower arm prosthetic system, including a lower arm stump having four prosthetic digits and a prosthetic thumb attached to the stump, and that includes an embodiment of a sensor assembly.

FIG. 1B is a side view of another example lower arm prosthetic system 101 including a lower arm portion 112 connected with four prosthetic digits 120 and a prosthetic thumb 130. The digits 120 may be connected to the end of the lower arm portion 112, as shown in FIG. 1B. The lower arm portion 112 may include an embodiment of the prosthetic wrist 104, the prosthetic lower arm 106, the prosthetic hand 102, or any combination thereof. In some cases, the prosthetic digits 120 and the prosthetic thumb 130 may be part of the prosthetic hand 102. The portion 112 may include the sensor assembly 202 attached to an inner surface thereof and contact a residual limb or a sound limb of a user when worn.

The prosthetic 101, prosthetic digits 120 and thumb 130 described herein are merely examples of prosthetics that may use the sensor assemblies of the present disclosure. Other prosthetic and orthotic systems may use the sensor assemblies described herein, for example the prosthetic and orthotic systems as described in U.S. Provisional Patent App. No. 62/950,843, titled ELECTROMYOGRAPHY AND MOTION BASED CONTROL OF UPPER LIMB PROSTHETICS and filed on Dec. 19, 2019, U.S. Provisional Patent App. No. 62/935,852, titled PROSTHETIC DIGIT ACTUATOR and filed on Nov. 15, 2019, U.S. Provisional Patent App. No. 63/064,614, titled PROSTHETIC DIGIT ACTUATOR and filed on Aug. 12, 2020, International Patent App. No. PCT/IB2020/054748, titled ACTUATION SYSTEMS FOR PROSTHETIC DIGITS and filed on May 19, 2020, International Patent App. No. PCT/IB2020/053373, titled PROSTHETIC DIGIT WITH ARTICULATING LINKS and filed on Apr. 8, 2020, International Patent App. No. PCT/IB2018/060072, titled POWERED PROSTHETIC THUMB and filed on Dec. 14, 2018, U.S. patent application Ser. No. 16/219,556, titled POWERED PROSTHETIC THUMB and filed on Dec. 13, 2018, U.S. patent application Ser. No. 16/204,059, titled SYSTEMS AND METHODS FOR PROSTHETIC WRIST ROTATION and filed on Nov. 29, 2018, U.S. patent application Ser. No. 15/508,064, titled WRIST DEVICE FOR A PROSTHETIC LIMB and filed on Mar. 1, 2017, U.S. patent application Ser. No. 15/307,385, titled SYSTEMS AND METHODS FOR CONTROLLING A PROSTHETIC HAND and filed on Oct. 28, 2016, each of which is hereby incorporated by reference herein in its entirety for all purposes and forms a part of this specification.

Figure 2A:
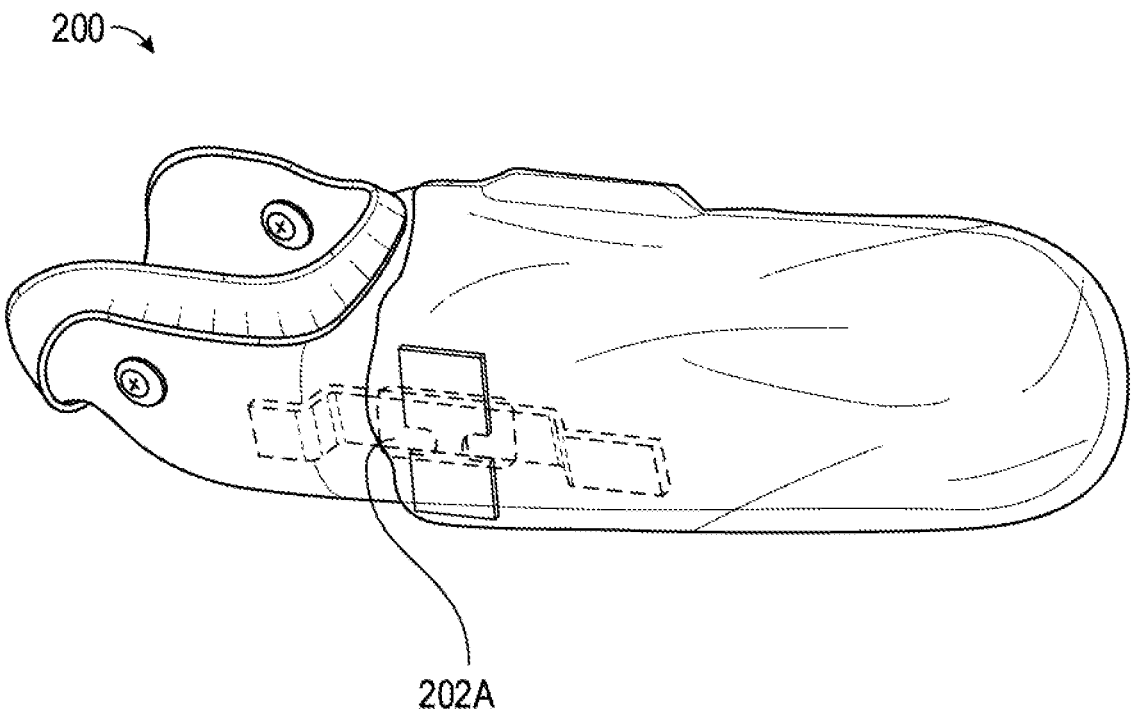
FIGS. 2A and 2B illustrate side perspective views of an embodiment of a fitting configured to attach to a POD and to a residual limb or a sound limb of a user of the POD and that includes an embodiment of the sensor assembly described herein.
Figure 2B:
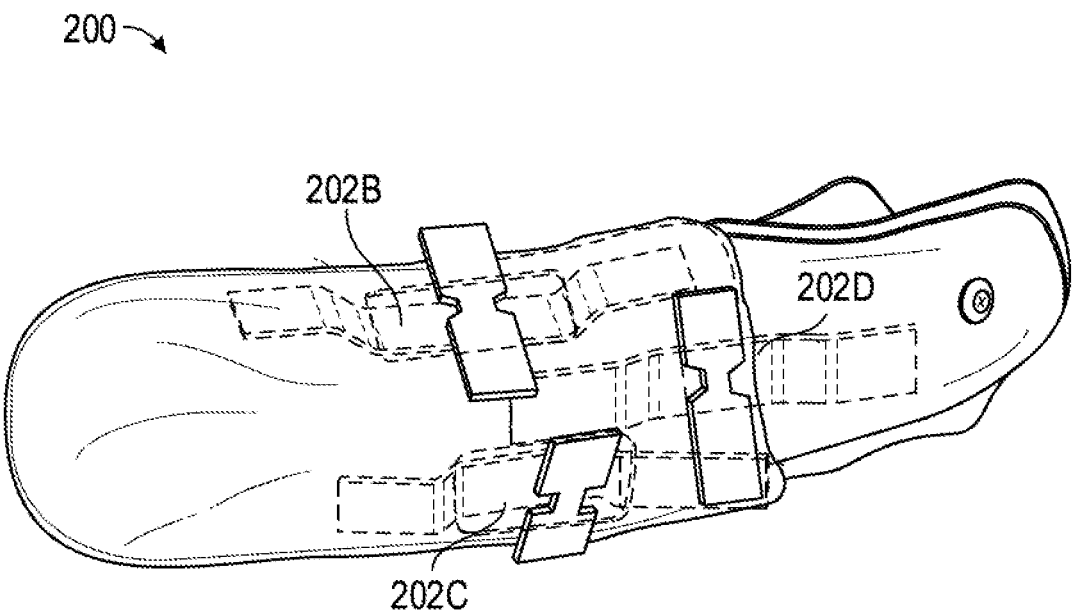

FIGS. 2A and 2B illustrate side perspective views of an example fitting 200 having embodiments of sensor assemblies 202A-202D. The fitting 200 is configured to attach to a prosthetic or orthotic device (POD) and a stump of a user of the POD. The fitting 200 may be formed of plastics, metals, composites, polymers, other suitable materials, or combinations thereof. As shown, the fitting 200 includes four sensor assemblies 202A, 202B, 202C, 202D (individually or collectively referred to as sensor assembly 202 or sensor assemblies 202). However, it will be understood that the number of sensor assemblies of the fitting 200 may vary across embodiments. There may be one, two, three, five, or more sensor assemblies 200, which may be attached to the same fitting 200, or some may be attached to other parts of a user, such as on a residual limb or a sound limb.

Each sensor assembly 202 is at least partially located on an internal side of the fitting 200 such that the sensor assembly 202 contacts a user's skin when the fitting 200 is worn on a stump. In instances in which the fitting 200 is worn on a trans-radial amputee forearm, the sensor assemblies 202 may be positioned in the fitting 200 such that they are generally aligned with the forearm muscles. For example, in some cases, the sensor assembly 202A contacts an internal side of the arm and is aligned with the forearm flexor muscles and the sensor assemblies 202B, 202C, and 202D contact an opposite, external side of the arm and are aligned with the forearm extensor muscles. The fitting 200 may extend axially and have a cavity defined therein by a sidewall and in which the one or more sensors 200 are located along inner surfaces of the sidewall. A proximal side of the fitting 200 may attach to a user and a distal side of the fitting 200 may attach to a prosthetic device.

Figure 3A:
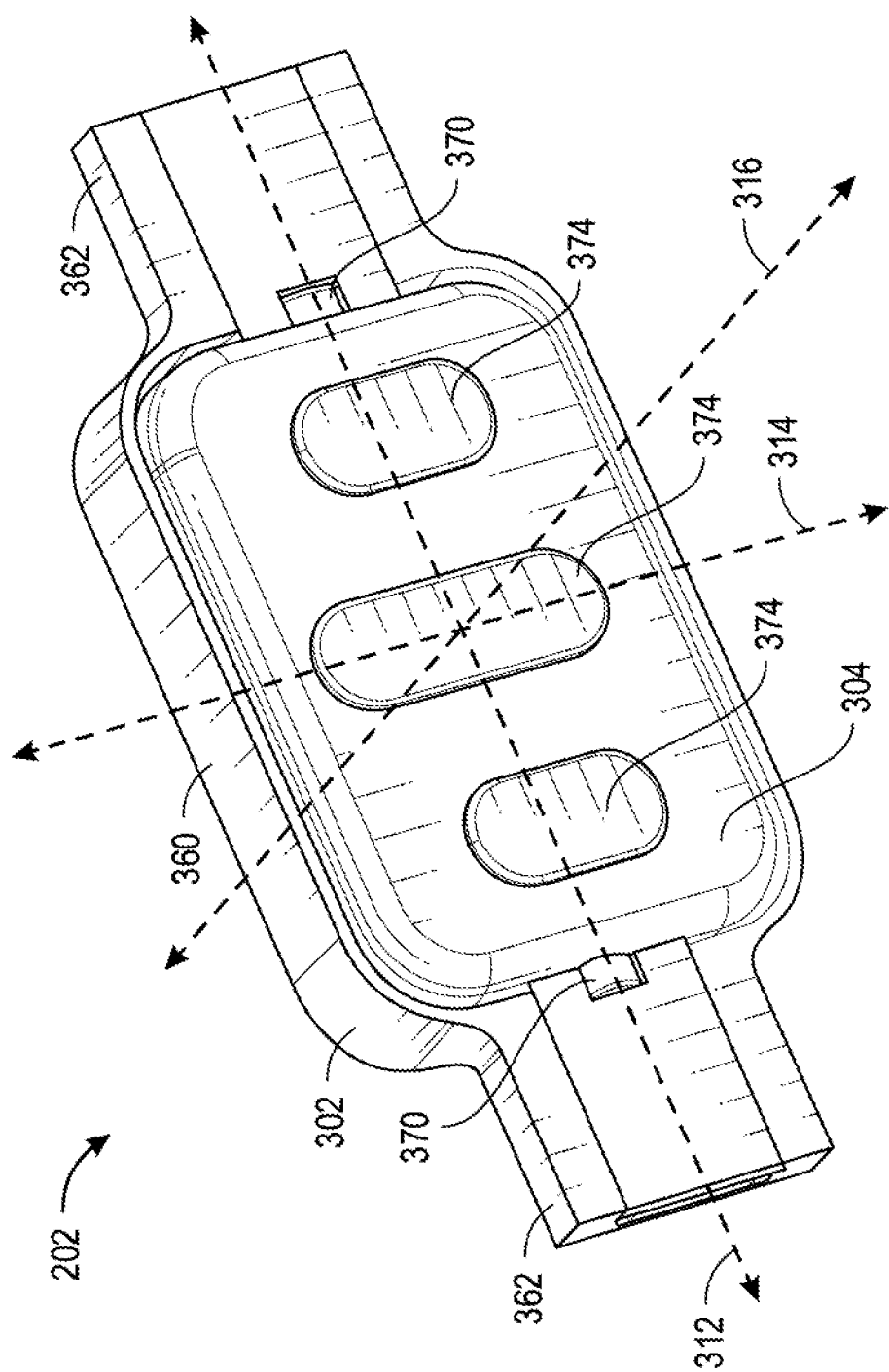
FIG. 3A is a perspective view of an embodiment of a sensor assembly.
Figure 3B:
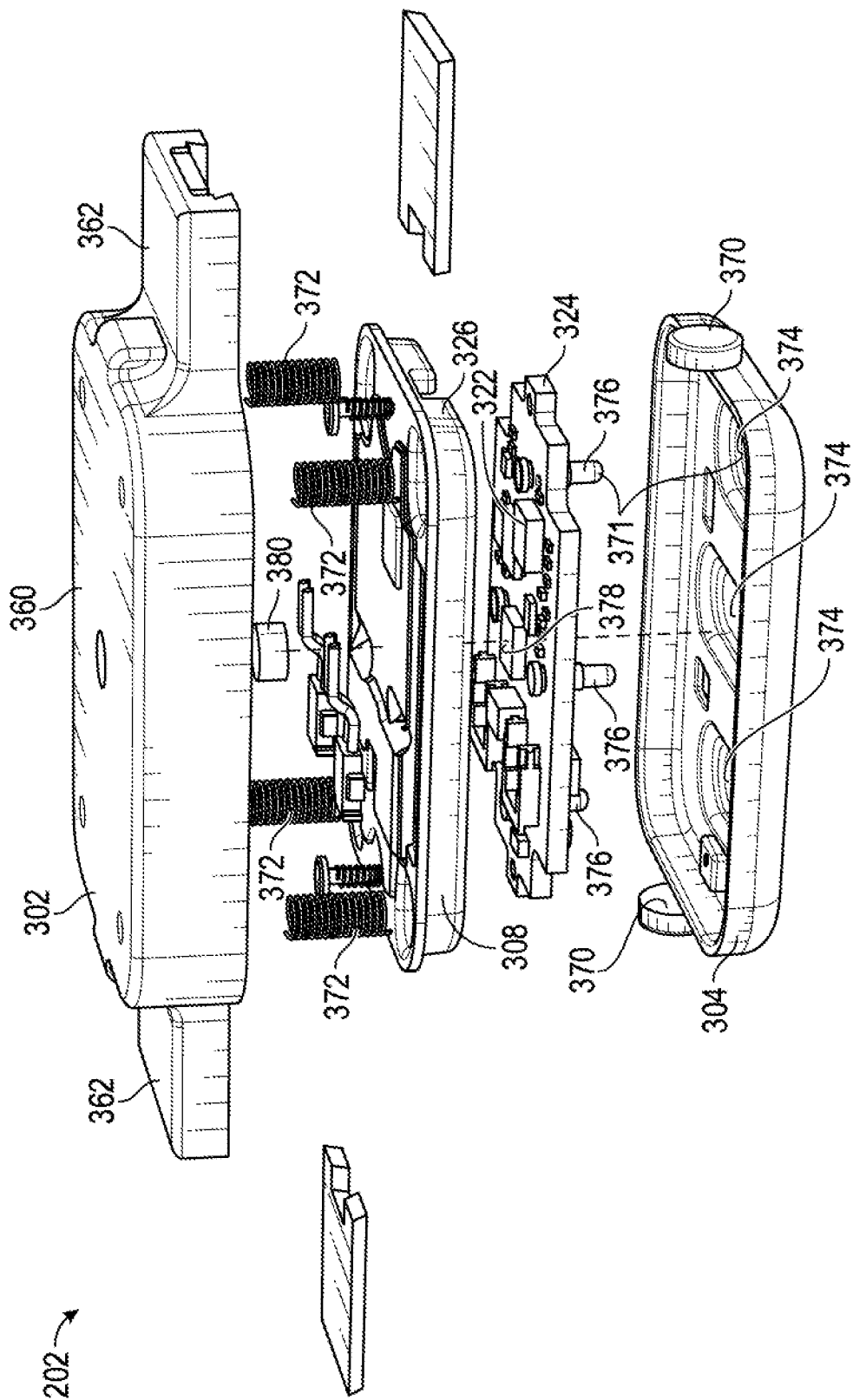
FIG. 3B is an exploded view of the sensor assembly of FIG. 3A.

FIG. 3A is a perspective view of the sensor assembly 202. FIG. 3B is an exploded view of the sensor assembly 202 of FIG. 3A. As described herein, one or more sensor assemblies 202 are configured to attach to a POD, such as the lower arm prosthetic system 100 of FIG. 1A or 1B, or a fitting that attaches to a POD, such as the fitting 200 of FIGS. 2A-2B. Further, any features or functions of the sensor assembly 202 may be incorporated into any other embodiments of sensor assemblies described herein, such as those shown in FIGS. 12A-18C, and vice versa.

The sensor assembly 202 includes an upper portion or housing 302, which forms a portion of an outer structure and enclosure of the sensor assembly 202. The housing 302 may be formed of plastics, metals, composites, polymers, other suitable materials, or combinations thereof. The housing 302 has a central portion 360 and a pair of end portions 362 on either end of the central portion 360. The central portion 360 may be rectangular as shown with the long end defining a longitudinal axis 312. The end portions 362 may be rectangular as shown. The housing 302 defines the longitudinal axis 312 extending along a length of the housing 302 and a lateral axis 314 extending along the width of the housing 302. The lateral axis 314 may be perpendicular to the longitudinal axis 312.

The sensor assembly 202 further includes a lower portion or support 304, which may be an overmold, and which forms a portion of the outer structure and enclosure of the sensor assembly 202. The support 304 may be formed of plastics, metals, composites, polymers, other suitable materials, or combinations thereof. The support 304 has a rounded rectangular shape and includes a pair cylindrical wing portions 370 on either end of the support 304.

The support 304 connects with the housing 302 to form the enclosure between the support 304 and the housing 302. The support 304 may be movably connected with the housing 302 such that the support 304 may translate and/or rotate relative to the housing 302. For example, the support 304 may be connected with the housing 302 such that it may move relative to the housing 302 along a central axis 316. The support 304 may be slidably connected to the housing 302 such that the support 304 may slide along the sliding axis or central axis 316. The central axis 316 may be perpendicular to the longitudinal axis 312 of the housing 302 and the lateral axis 314 of the housing 302.

In some embodiments, movement of the support 304 relative to the housing 302 is caused by user movement applying a compressive force toward the sensor assembly and compressing at least one biasing member located between the support 304 and the housing 302. For example, FIG. 3B illustrates four biasing members 372 that bias the support 304 in a direction away from the housing 302 and toward the user. In this example, the biasing members 372 are illustrated as compression springs. However, other biasing members are contemplated, such as flexible members, extension springs, other suitable biasing members, or combinations thereof. The biasing members 372 thus pre-load the support 304 so that it contacts the user. The biasing members 372 then compress in response to outward movement of the user's limb and/or muscle, and thereby allow relative movement of two portions of the sensor assembly. This relative movement is detected by one or more of the sensors and analyzed for prosthetic control, as further described herein.

In some cases, the support 304 is additionally or alternatively pivotably connected to the housing 302 such that the support 304 may be pivoted or partially rotated about one or more pivot axes. The pivot axis or axes may align with the longitudinal, lateral and/or central axes 312, 314, 316. For example, in some cases, the projections 370 of the support 304 may engage with a complementary engagement cavity of the housing 302. The projections may be cylindrical and extend longitudinally away from the support 304. In some embodiments, the projections 370 act as a hinge and the pivot axis may correspond to an axis that that extends between the centers of the projections 308. In some cases, the pivot axis aligns with the longitudinal axis 312 of the housing 302. The pivot axis may be substantially parallel to the longitudinal axis 312 of the housing 302, substantially perpendicular to the lateral axis 314 of the housing 302, and/or substantially perpendicular to the central axis 316. In some cases, the support 304 may be both slidably and pivotably connected to the housing 302 such that the support 304 may move along the sliding axis and be pivoted about the pivot axis or axes. In some such cases, the location of the pivot axis may be dependent upon the position of the support 304, for example along the lateral axis 314 and/or other axes.

The sensor assembly 202 may further include one or a plurality of sensors. The plurality of sensors may include, but are not limited to, an inertial measurement unit (IMU) 322, an electromyography (EMG) sensor 371, or a magnetic sensor 378, such as a Hall effect sensor. The magnetic sensor may be a device for detecting and measuring magnetic fields. In some embodiments, the magnetic sensor 378 may be any of a variety of distance or displacement sensors that senses displacement, such as a change in position and/or orientation, of the user's muscle relative to a starting position and/or orientation of the muscle. The sensor assembly 202 may further include a circuit board 324. The circuit board 324 may be in electrical communication with the plurality of sensors to receive sensor data. The sensor assembly 202 may further include a tray 326, as further described.

The IMU 322 may detect velocities, accelerations, angular rates, orientations, and other movements of the limb of the user. The IMU 322 may detect a vibromyography (VMG) signal associated with a muscle of the user. The IMU 322 may be coupled to and in electrical communication with the circuit board 324. The IMU 322 may include at least one of an accelerometer, a gyroscope, or a magnetometer. The IMU 322 may include an accelerometer, a gyroscope, and/or a magnetometer. The IMU 322 may include only an accelerometer and a gyroscope. In some cases, the IMU 322 can be used as a motion sensor or absolute orientation sensor. For example, the IMU 322 can be implemented as a 9-axis IMU (e.g., 3-axis gyroscope; 3-axis accelerometer; 3-axis magnetometer).

The EMG sensor 371 may include one or more EMG pickups 374 carried by the support 320. In this way, the one or more EMG pickups 374 move with the support 320 as the support 320 moves (e.g., moving along the sliding axis and/or pivoting about the pivot axis). The one or more EMG pickups 374 are configured to contact skin of a user. For example, an outer surface of the support 320 and the one or more EMG pickups 374 may be configured to contact the residual limb or the sound limb of the user. The EMG sensor also includes one or more electrical contacts 376 coupled to the circuit board 324 and extending downward therefrom to contact the EMG pickups 374 when assembled. The contacts 376 and EMG pickups 374 may detect EMG signals and communicate the signals to the circuit board 324.

The magnetic sensor 378 may detect or measure one or more magnetic fields. In some cases, the magnetic sensor 378 may detect the mechanical response of a muscle of the user during movement of the muscle. For example, muscle movement may be read by magnetic flux proximity and direction from a magnet 380 to the magnetic sensor 378. The magnet 380 may generate a magnetic field and the magnetic sensor 378 may detect the magnetic field generated by the magnet 380. The magnet 380 may be attached with the housing 302. The magnetic sensor 378 may be implemented as a Hall effect sensor or magnetometer. The magnetic sensor 378 may be attached with the circuit board 324 or the support 320. In some cases, the magnetic sensor 378 and the magnet 380 are separated by a set distance. In some embodiments, the magnetic sensor 378 may be replaced by an MMG sensor or any type of distance or displacement sensor or detector that detects the distance between the housing 302 and the support 304. For example, a visual sensor such as LIDAR, etc. may be used to detect the variable distance.

The sensor assembly 202 may further include the tray 326. The tray may be positioned between the support 304 and the housing 302. As shown, the tray 326 may be attached to the support 304 and may be moveably attached with the housing 302. For example, ends of the biasing member 372 may be coupled to the tray 326 housing 302. In some cases, the tray 326 is pivotably and/or slidably connected to the housing 302. For example, the tray 326 may move as the support 304 moves. The circuit board 324 may be located underneath the tray 326 as shown, or the circuit board 324 may be in other locations, such as above the tray 326.

Figure 4A:
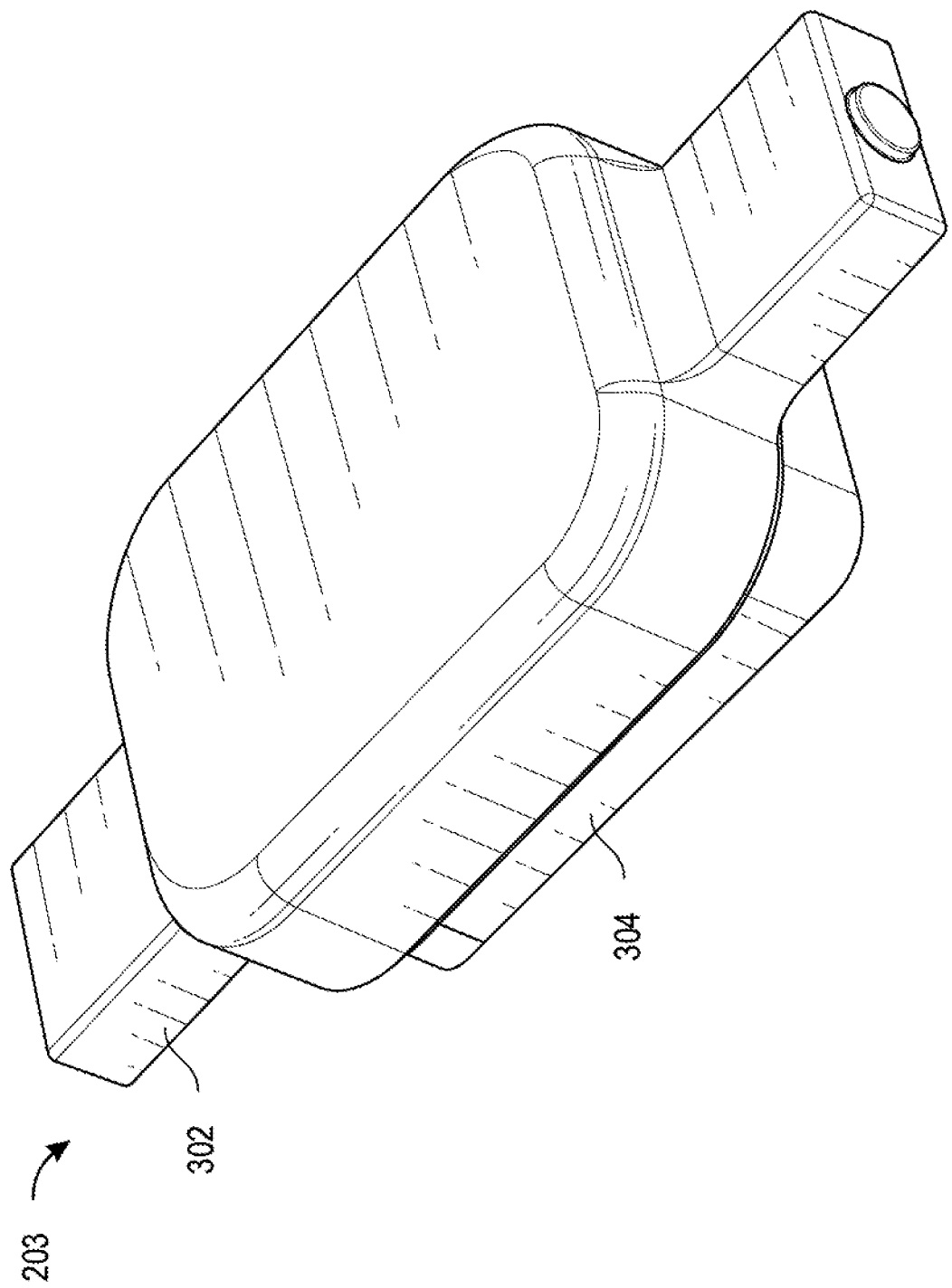
FIG. 4A is a perspective view of another embodiment of a sensor assembly.
Figure 4B:
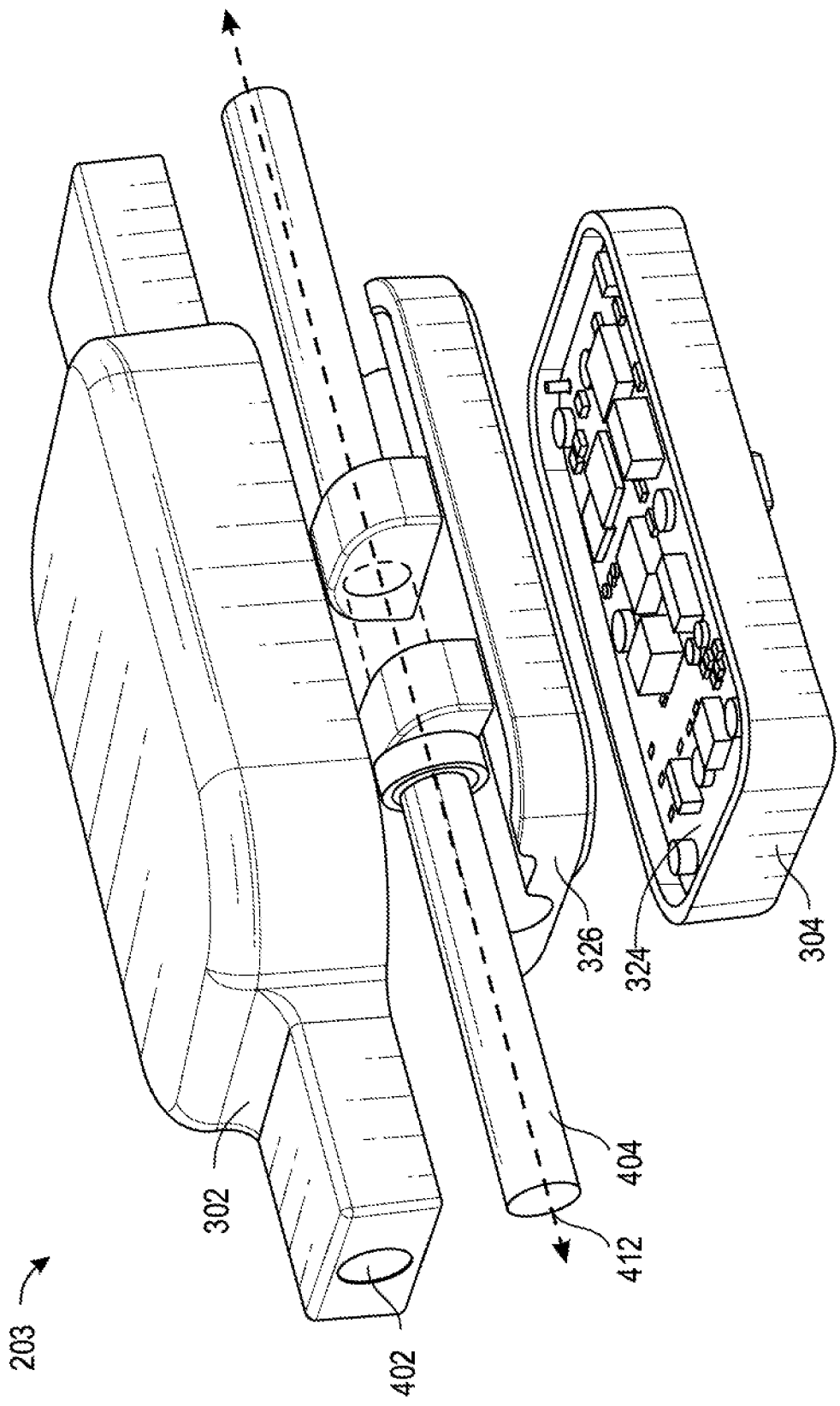
FIG. 4B is an exploded view of the sensor assembly of FIG. 4A.
Figure 4C:
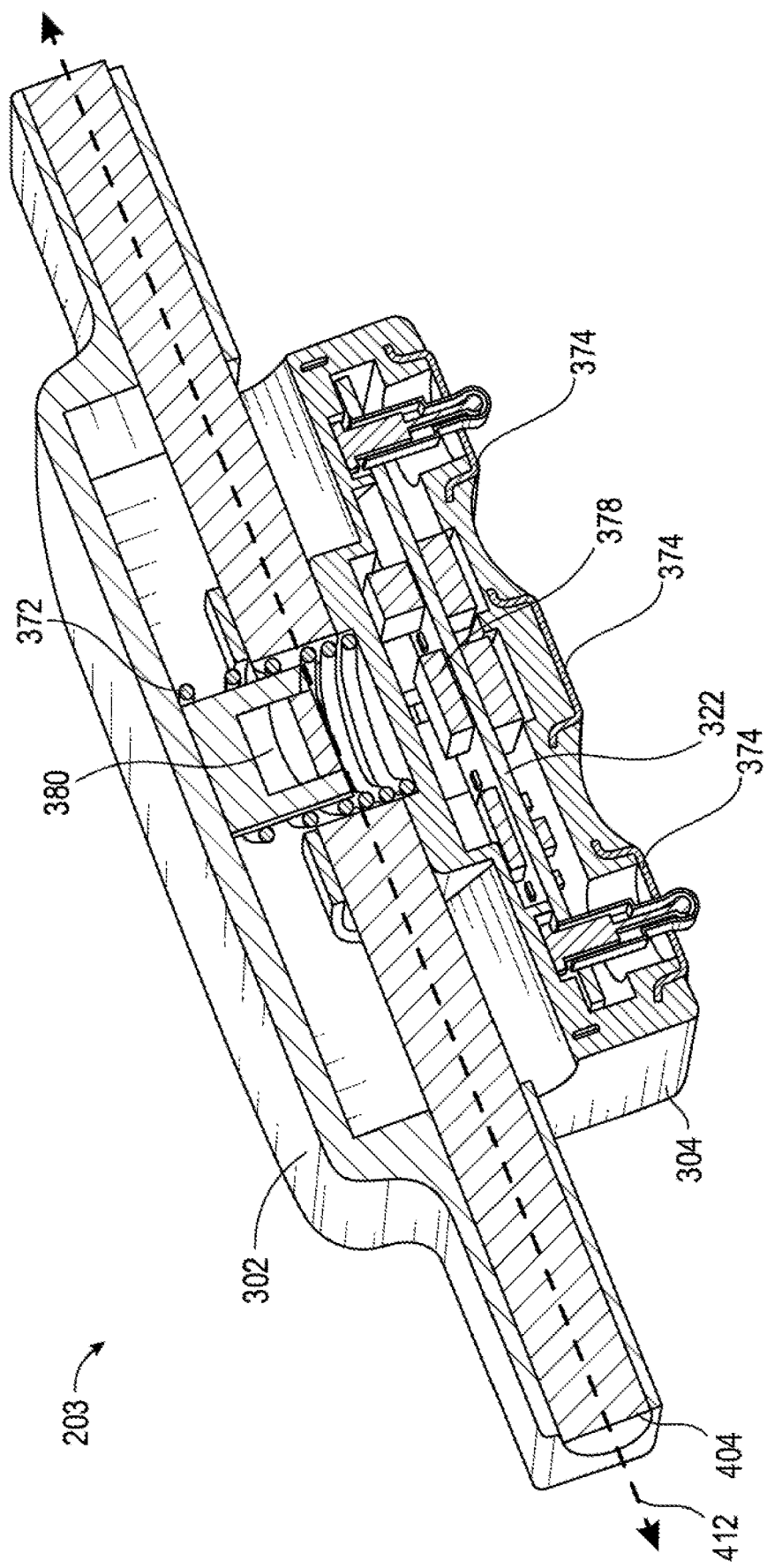
FIG. 4C is a cross-sectional view of the sensor assembly of FIG. 4A.

FIG. 4A is a perspective view of another embodiment of a sensor assembly 203. FIGS. 4B and 4C show an exploded view and a cross-sectional view, respectively, of the sensor assembly 203. The sensor assembly 203 may have the same or similar features and/or functions as the sensor assembly 202, and vice versa, except as otherwise described. Further, any features or functions of the sensor assembly 203 may be incorporated into any other embodiments of sensor assemblies described herein, such as those shown in FIGS. 12A-18C, and vice versa.

As illustrated in FIGS. 4A-4C, the sensor assembly 203 may include the housing 302, the support 304, the circuit board 324, the tray 326, the biasing member 372, and the plurality of sensors. The plurality of sensors may include an IMU 322, an EMG sensor (EMG pickups 374), and a magnetic or sensor 378. The EMG pickups 374 may extend below the lower plane of the support 304 when assembled. In some embodiments, the electrical connects 376 may extend below this plane. The EMG sensor may thus ensure contact with the skin in this manner.

The sensor assembly 203 also includes an axle 404. The axle 404 may be an elongated structural member extending longitudinally, for example parallel to the longitudinal axis. The axle 404 may be cylindrical, and by solid or hollow. The axle 404 may facilitate a pivoting movement of the support 304 relative to the housing 302. For example, the axle 404 may engage with complementary engagement cavities 402 located at longitudinal ends of the housing 302. In some such cases, the axle 404 acts as a hinge such that the support 304 may pivot about a pivot axis 412 that is centered along the axle 404. In some cases, the pivot axis 412 is the longitudinal axis of the housing 302. The pivot axis 412 may be substantially parallel to the longitudinal axis of the housing 302 or substantially perpendicular to a lateral axis of the housing 302.

Figure 5A:
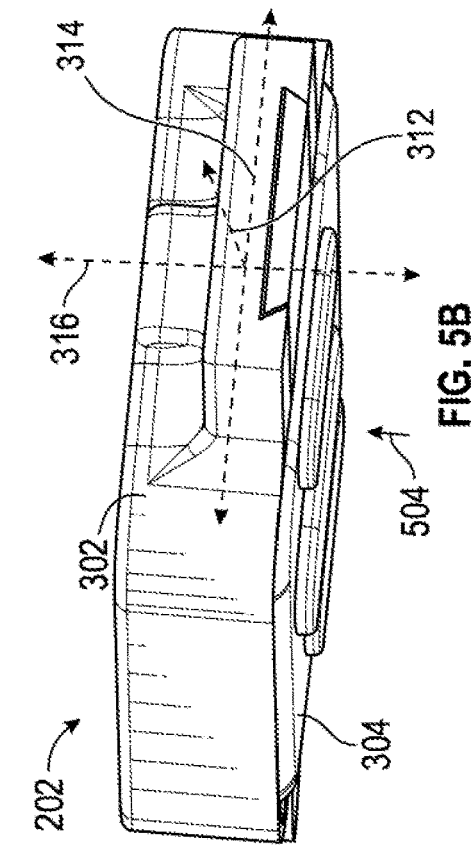
FIGS. 5A-5D illustrate various configurations of an example sensor assembly showing a lower portion or support of the assembly in various orientations relative to the upper portion or housing.
Figure 5B:
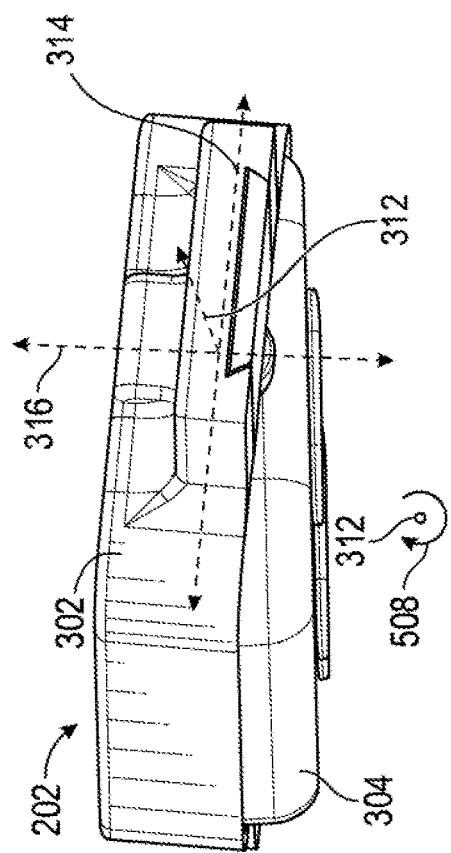

FIGS. 5A-5D illustrate various configurations of the sensor assembly 202. The various configurations of the sensor assembly 202 described with respect to FIGS. 5A-5D may apply to the other embodiments of the sensor assemblies described herein such as the sensor 203, the sensor assemblies shown in FIGS. 12A-18C, etc. As described herein, the support 304 may be slidably connected to the housing 302 such that the support 304 may be slid, shifted, pushed, or otherwise translated along the central axis 316 (sometimes referred to as the sliding axis). FIGS. 5A and 5B illustrate example orientations of the sensor assembly 202 in which the support 304 has been shifted along the central axis 316. In particular, FIG. 5A illustrates the support 304 shifted along the central axis away from the housing 302 in a first proximal direction 502, and FIG. 5B illustrates the support 304 shifted along the central axis towards the housing 302 in a second distal direction 504. In some cases, the position of the support 304 illustrated in FIG. 5A may be a default resting position of the support 304. For example, at least one biasing member may be disposed between the housing 302 and the support 304 and may bias the support 402 in the first direction 502 (or bias the housing 302 in the second direction 504). The range of motion of the support 304 along the central axis 316 may vary across embodiments. For example, the range of motion of the support 304 along the central axis 316 may be limited by mechanical end stops of the housing 302 or the support 304.

Figure 5C:
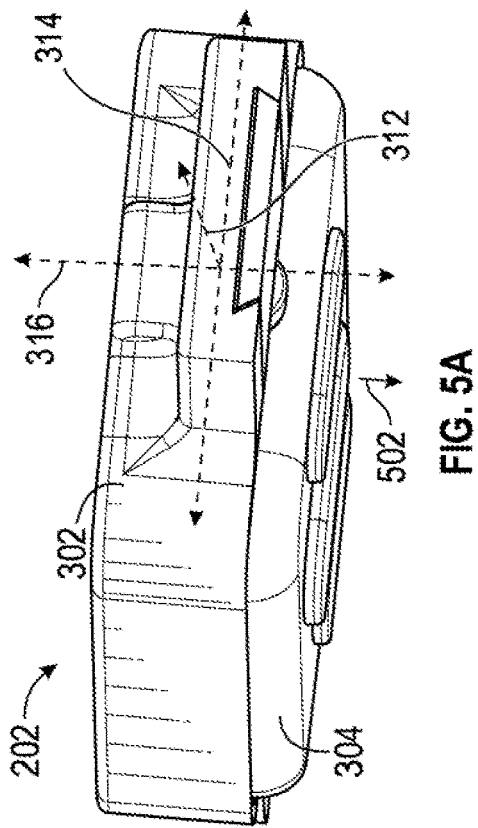
Figure 5D:
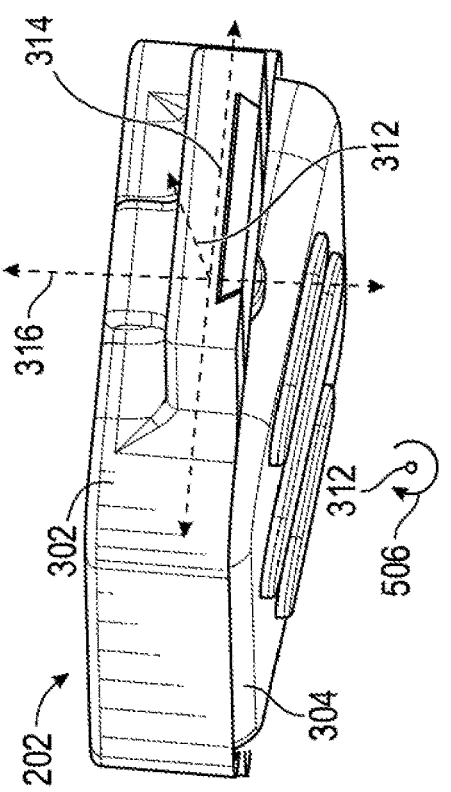

The support 304 may be pivotably connected to the housing 302 such that the support 304 may be pivoted or partially rotated about a pivot axis. FIGS. 5C and 5D illustrate example orientations of the sensor assembly 202 in which the support 304 has been pivoted about the longitudinal axis 312 of the housing 302. In particular, FIG. 5C illustrates the support 304 rotated about the longitudinal axis 312 in a third rotational direction 506, where the third rotational direction 506 corresponds to a counterclockwise direction as oriented in the figure, and FIG. 5D illustrates the support 304 rotated about the longitudinal axis 312 in a fourth rotational direction 508, where the fourth direction 508 corresponds to a clockwise direction as oriented. The support 304 may also pivot about the lateral axis 314 in a similar manner as described with respect to rotation about the longitudinal axis 312.

The sensor assembly 202 thus provides for movement of the support 304 relative to the housing 302 with multiple degrees of freedom. The support 304 may have any or all of the various degrees of freedom described herein. For example, the support 304 may have three degrees of freedom including translation along the longitudinal and central axes 312, 316 as well as rotation about the longitudinal axis 312. In some embodiments, the support 304 may have one, two, three, four, five, or six degrees of freedom. For example, the support 304 may in addition translate along the lateral axis 314 and/or rotate about the lateral and/or central axes 314, 316. The plurality of degrees of freedom of movement of the support 304 relative to the housing 302 enhances tracking of the user's limb and increases accuracy of the detected electrical and mechanical signals. In some embodiments, the support 304 may only translate axially along a single axis relative to the housing 302, and not rotate about any axis or translate about any other axis.

As shown, when rotated or pivoted about the pivot axis (which, in this case is the longitudinal axis 312), one side of the support 304 moves further away from the housing 302 while the other side of the support 304 moves closer to the housing 302. This movement causes a volume or area of the enclosure between the support 304 and the housing 302 to expand on one side of the sensor assembly 202 (i.e., the side at which the support 304 moves further away from the housing 302) and reduce on the other side of the sensor assembly 202 (i.e., the side at which the support 304 moves closer from the housing 302).

The permitted movement of the support 304 between the various orientations shown in FIGS. 5A-5D allows the support 304 to move congruously with the residual limb or the sound limb to ensure good contact with the residual limb or the sound limb is maintained. In this way, the sensor assembly 202 increases the likelihood that one or more of the plurality of sensors of the sensor assembly 202 may maintain a reliable contact with the skin and thus provide a reliable signal. For example, consistent contact between the sensor assembly 202 and the residual limb or the sound limb may aid in the EMG sensor in maintaining a reliable signal, may ensure the magnetic sensor accurately tracks movement of the muscle, etc.

Figure 6:
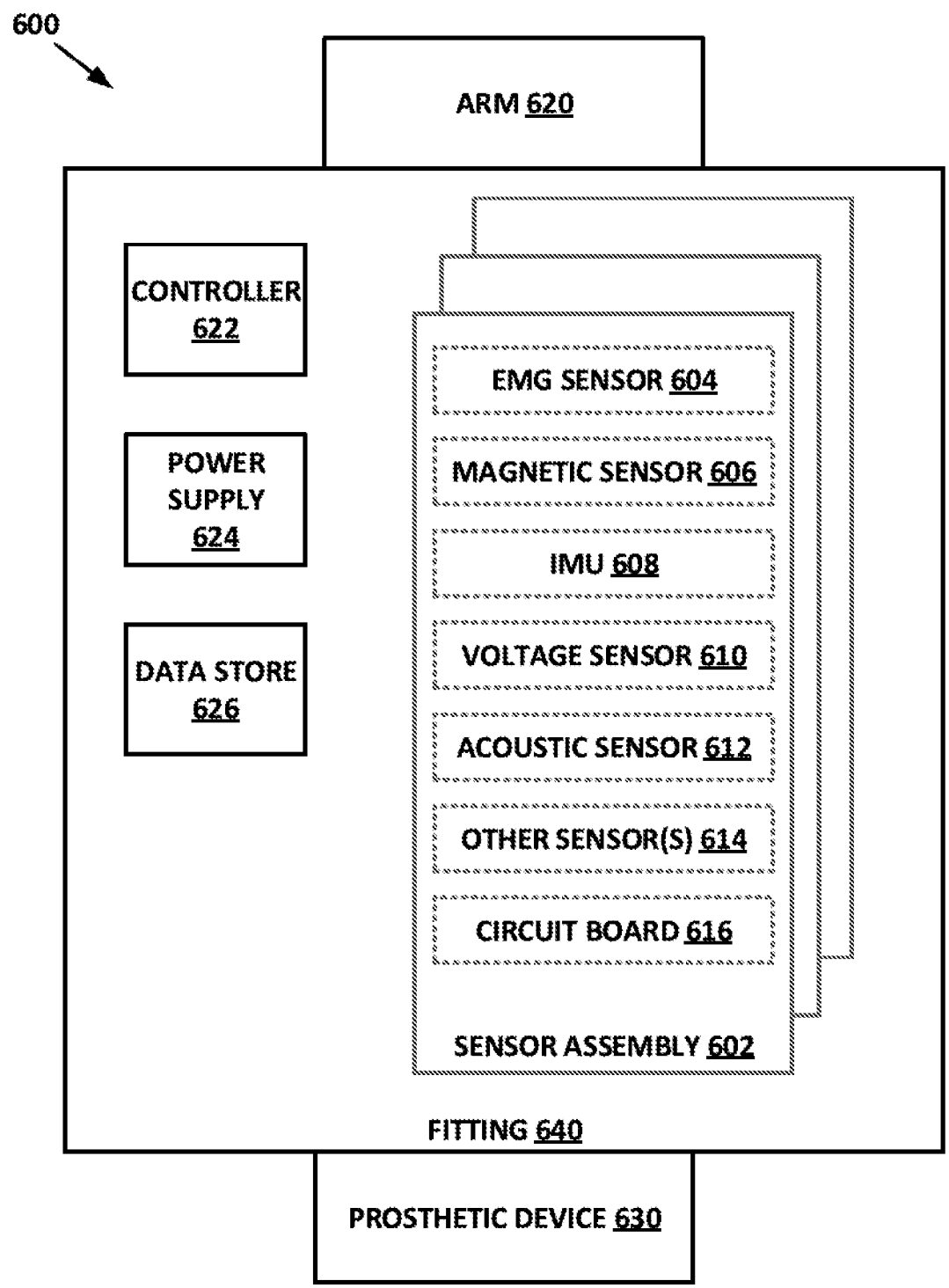
FIG. 6 is a block diagram showing a schematic of an example prosthetic system having the sensor assembly.

FIG. 6 illustrates a block diagram of an example prosthetic system 600 including a sensor assembly 602. The sensor assembly 602 may have the same or similar features and/or functions as any of the embodiments of the sensor assemblies described herein, such as the sensors 202, 203, etc., and vice versa. In the illustrated example, the prosthetic system 600 includes an arm 620 attached to a fitting 640. The prosthetic system 600 also includes a prosthetic device 630 attached to the fitting 640. The prosthetic system 600 may be an embodiment of the lower arm prosthetic system 100 of FIG. 1A or 1B. The fitting 640 may be an embodiment of the fitting 200 of FIG. 2A or 2B. The prosthetic device 630 may be an embodiment of one or more of the prosthetic hand 102, the prosthetic wrist 104, the prosthetic lower arm 106, the lower arm stump 112, or the prosthetic digits 120 of FIG. 1A or 1B.

The arm 620 may be a prosthetic arm or may be a natural arm, i.e. a natural or sound human arm, or a stump. The fitting 640 may be attached to a distal end of the arm 620. The prosthetic device 630 may be a prosthetic arm or hand attached to the fitting 640.

The prosthetic system 600 may include a controller 622, a power supply 624, a data store 626, and one or more of the sensor assemblies 602. Although illustrated as being part of the fitting 640, any one or more of the controller 622, power supply 624, data store 626, or sensor assembly 602 may be located in a number of locations including any location in or on the prosthetic device 630, remote from the fitting 640 or the prosthetic device 630 or the like. Furthermore, it will be understood that some of the separate components may be combined in a variety of ways to achieve particular design objectives. For example, in some cases, the fitting 640 may be combined with the prosthetic device 630. As another example, the data store 626 may be combined with controller 622 components to save cost and/or improve performance.

The sensor assembly 602 may be an embodiment of the sensor assembly 202 described herein. The sensor assembly 602 can be configured to sense muscle activity. For example, the sensor assembly 602 can include one or more sensors that are sensitive to force, distance/displacement, potential difference (e.g., voltage), vibrations, sound/acoustic readings, or another symptom of muscle activity. As another example, the sensor assembly 602 may include any one or any combination of an EMG sensor 604, a magnetic sensor 606, an IMU 608, a voltage sensor 610, an acoustic sensor 612, or one or more other sensors 614. Furthermore, the sensor assembly 602 may include a circuit board 616, such as the circuit board 324 of FIG. 3B.

Data from the sensor assembly 602 (e.g., data from the EMG sensor 604, magnetic sensor 606, IMU 608, the voltage sensor 610, the acoustic sensor 612, or the one or more other sensors 614) may be received by the circuit board 614 or the controller 622 and may be used to determine various parameters associated with the prosthetic system 600. For example, the controller 622 may translate input signals (e.g., an EMG signal, a magnetic field signal, distance signal, an IMU signal, etc.) received from the sensor assembly 602 into a prosthetic movement. For example, the data store 626 may store an operating profile that includes a plurality of hand gestures or hand grips. The operating profile may associate each of the plurality hand gestures or hand grips with a corresponding input signal, set of input signals, or combination of input signals such that the controller 622 may select a hand gesture or a hand grip from the operating profile based at least in part on the input signals.

FIG. 7 is a table 700 illustrating various example associations between input signals and hand gestures or hand grips. The various associations and control techniques may be used with any of the embodiments of sensor assemblies described herein. The table 700 includes four columns: user movement, muscle contraction, forearm rotation, and classification. The "user movement" column includes images showing a sound hand/arm performing a particular hand gesture or hand grip. The "muscle contraction" column illustrates various input signals associated with each of four measurement sites: Site 1 (fitted to the internal side of the arm aligned with the forearm flexor muscles), Sites 2-4 (fitted to the external side of the arm aligned with the forearm extensor muscles). The "forearm rotation" column illustrates the forearm movement associated with the particular hand gesture or hand grip. The "classification" column is an identifier of the hand gesture or a hand grip, such as the name to which it is commonly referred.

The first row 702 of the table 700 corresponds to the hand gesture "hand open." As indicated by the muscle contraction and forearm rotation columns, the controller 622 will translate input signals at Site 1 and no forearm rotation into this hand gesture. The second row 704 of the table 700 corresponds to the hand gesture "hand close." As indicated by the muscle contraction and forearm rotation columns, the controller 622 will translate input signals at Site 3 and no forearm rotation into this hand gesture. The third row 706 of the table 700 corresponds to the hand gesture "wrist supination." As indicated by the muscle contraction and forearm rotation columns, the controller 622 will translate input signals across Sites 1-4 and a clockwise forearm rotation into this hand gesture. The third row 706 of the table 700 corresponds to the hand gesture "wrist pronation." As indicated by the muscle contraction and forearm rotation columns, the controller 622 will translate input signals across Sites 1-4 and a counter clockwise forearm rotation into this hand gesture.

Figure 8:
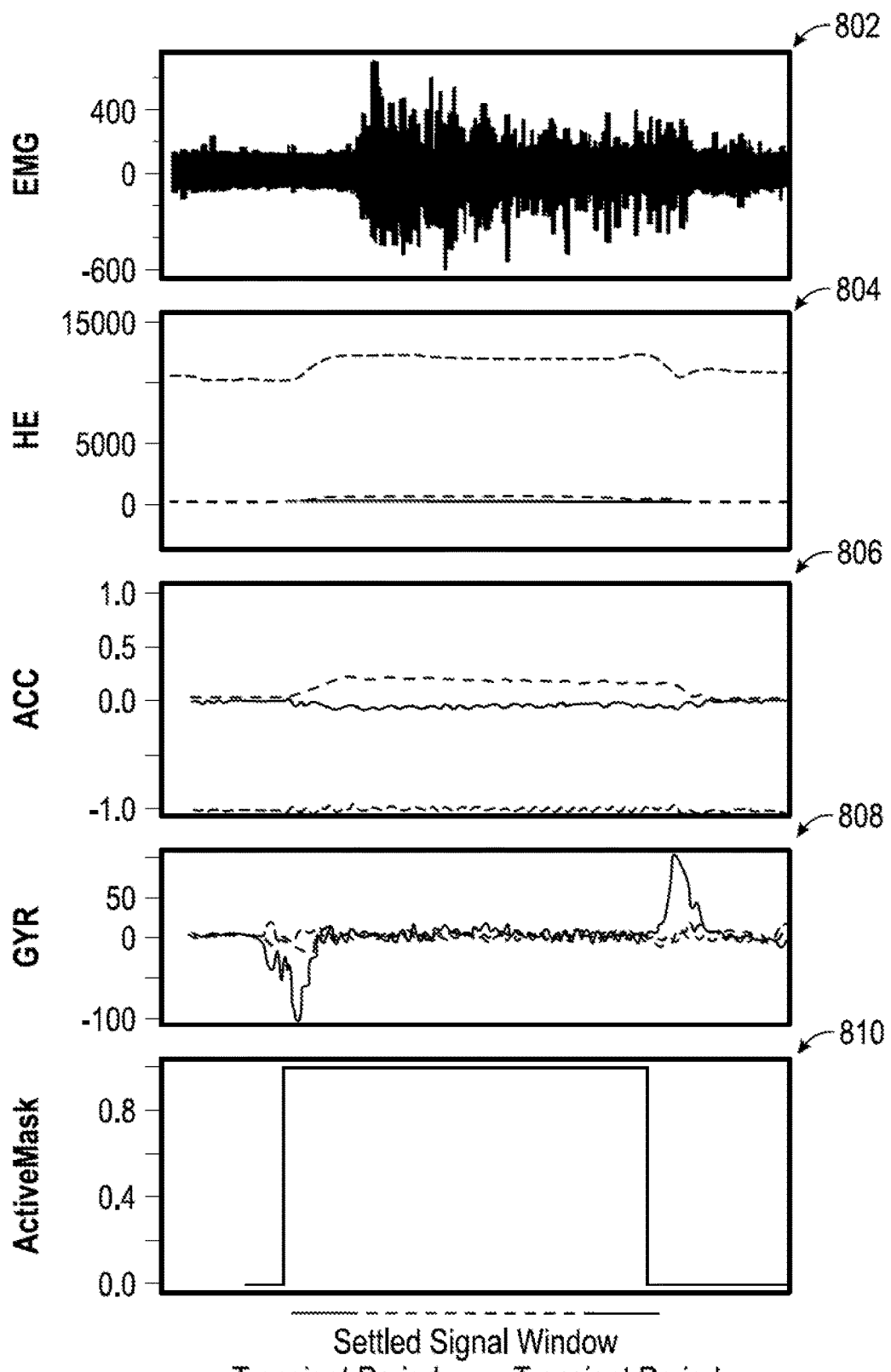
FIG. 8 illustrates example data graphs of various example input signals detected by the sensor assembly.

FIG. 8 illustrates graphs of various example input signals. In particular, FIG. 8 illustrates an EMG graph 802, an MMG graph 894, an accelerometer graph 806, a gyroscope graph 808, and an active mask graph 810.

Figure 9A:
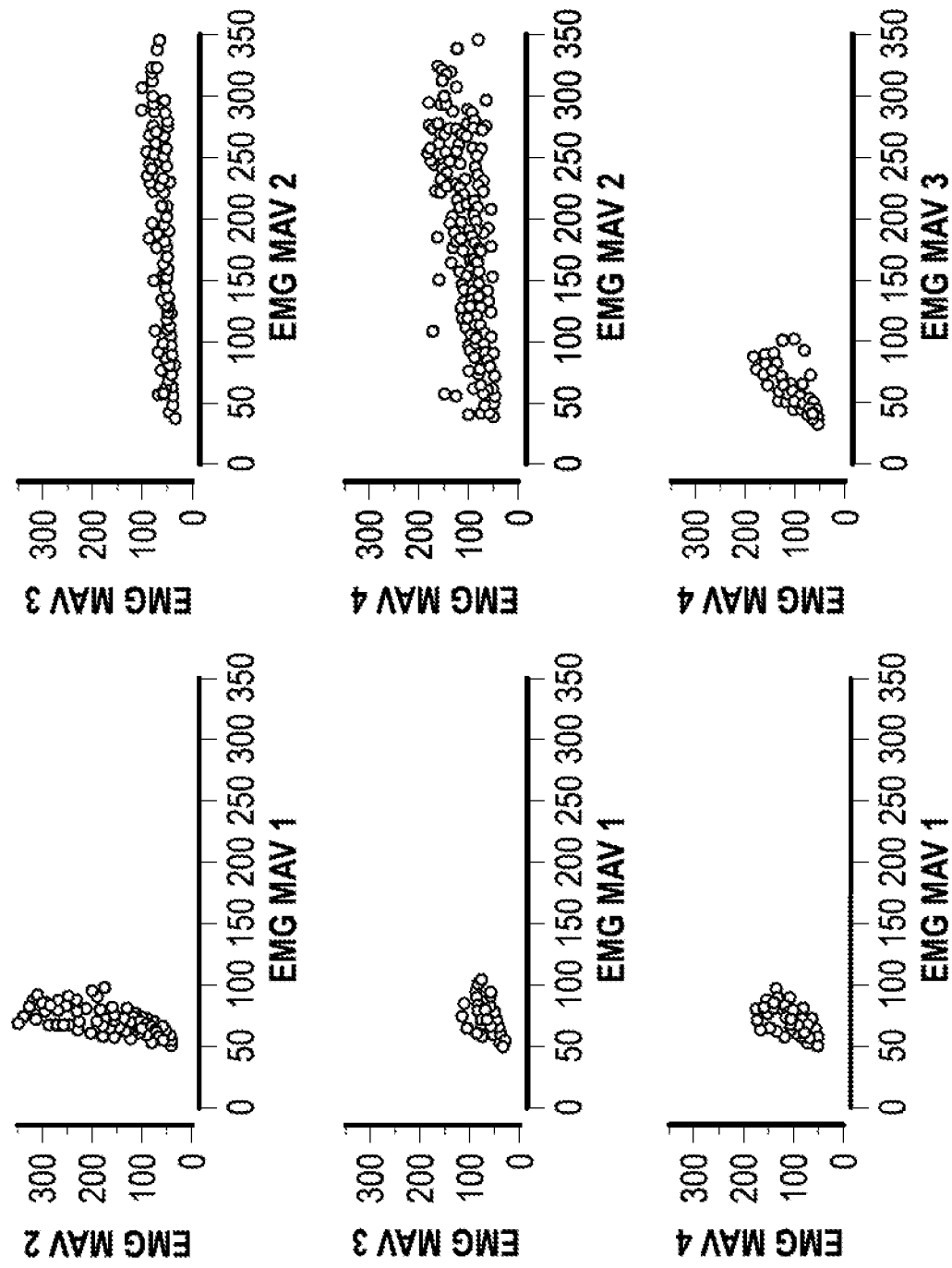
FIGS. 9A-9D illustrate example data graphs of various example data received from an example sensor assembly.
Figure 9B:
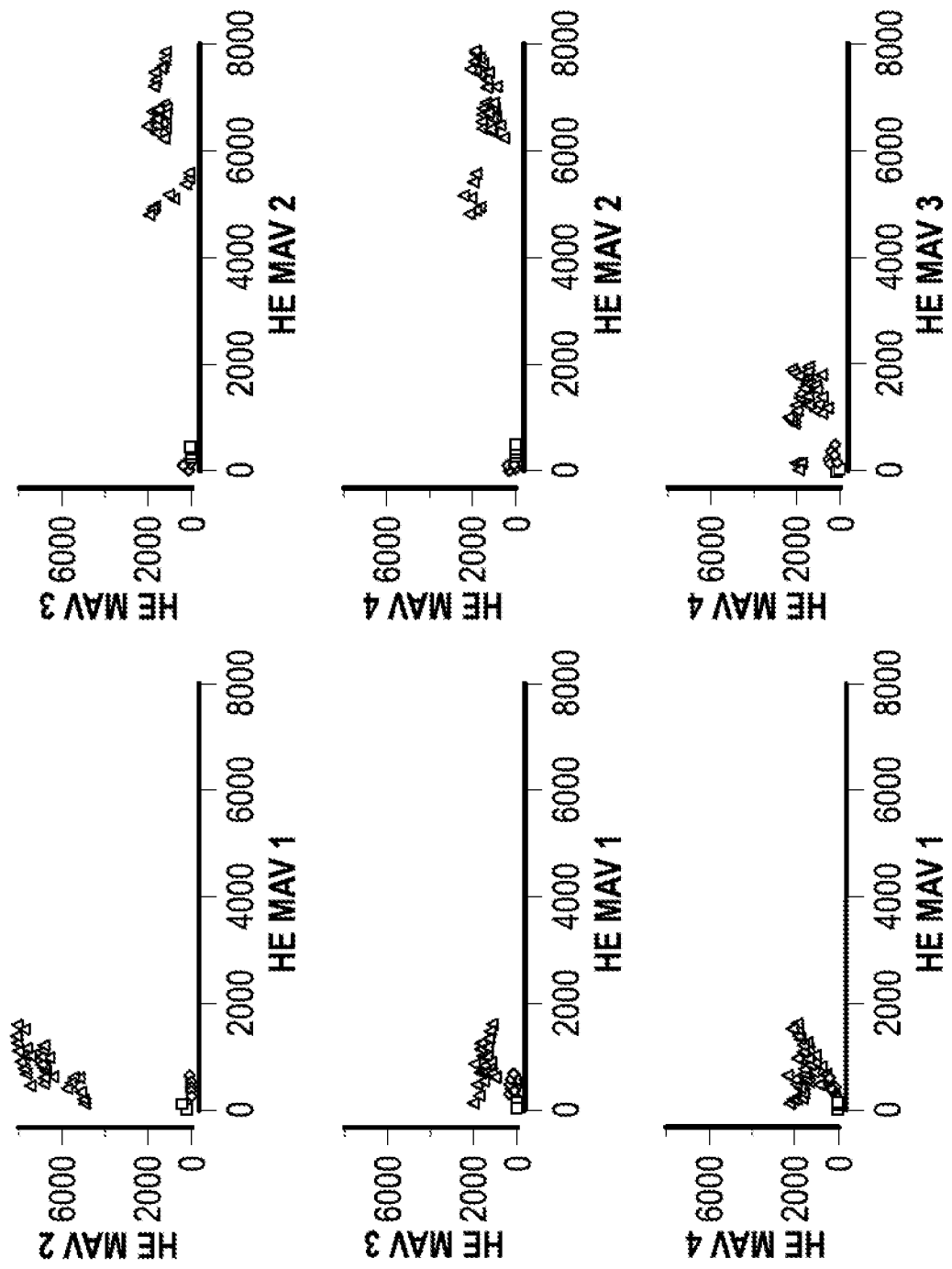
Figure 9C:
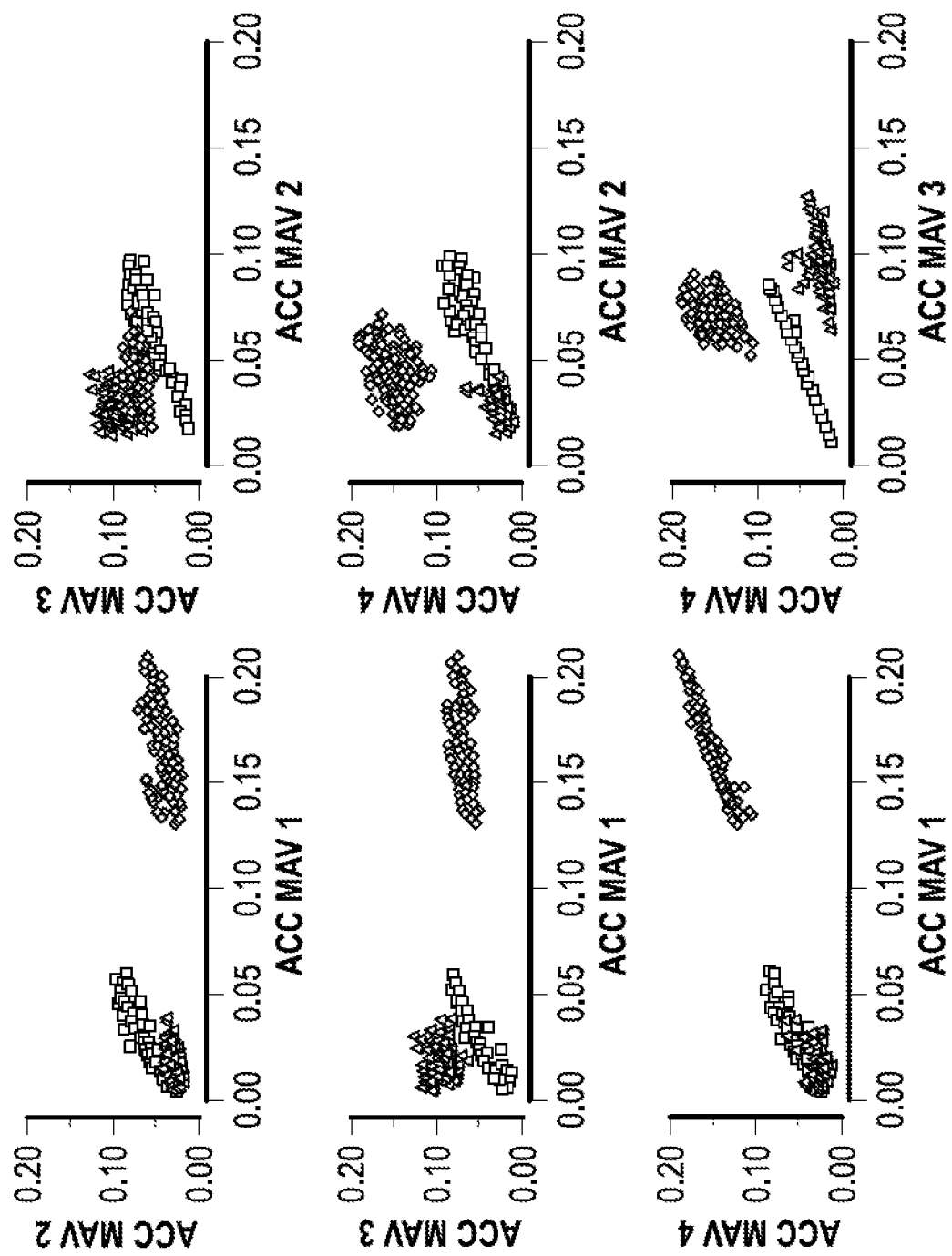
Figure 9D:
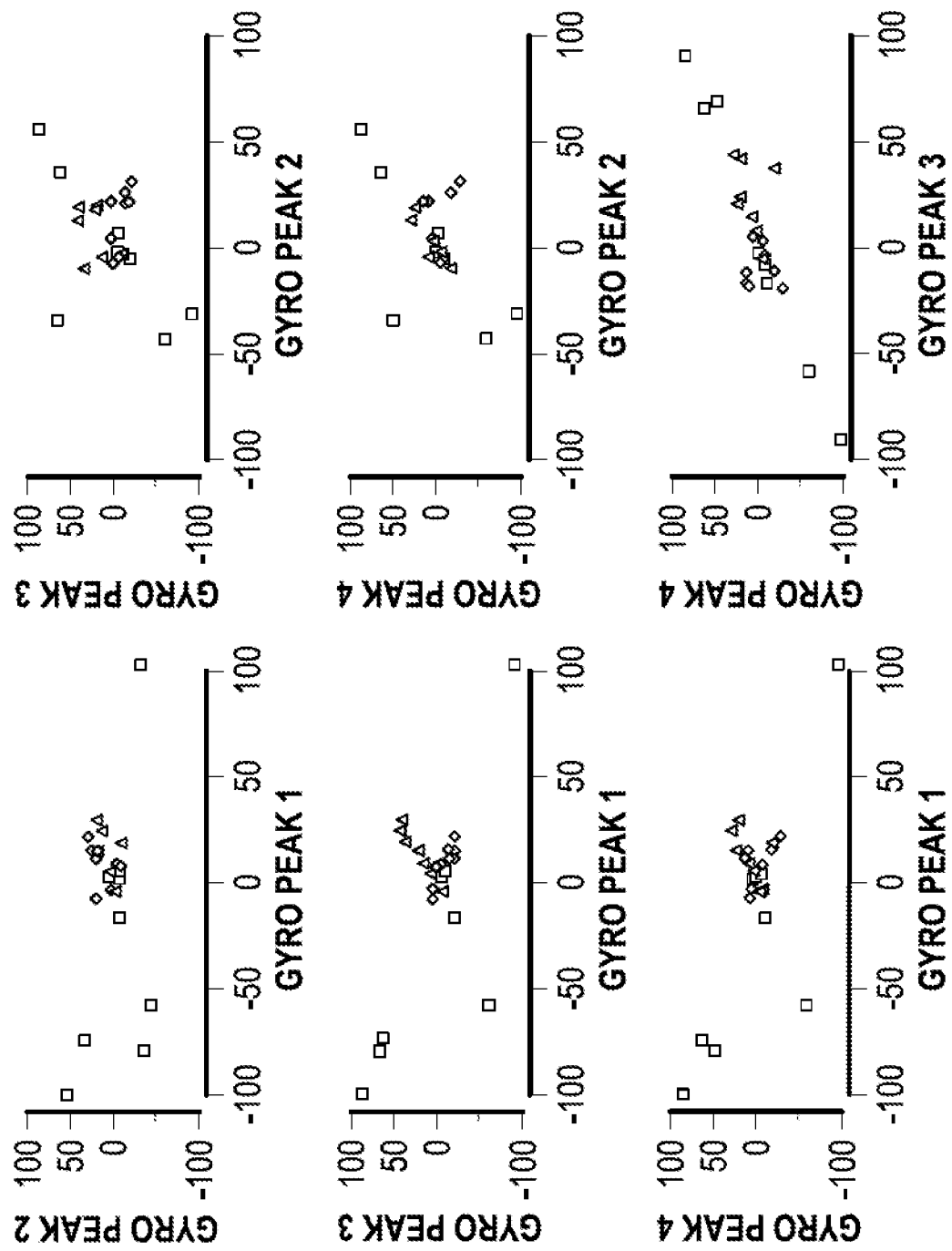

FIGS. 9A-9D illustrate graphs of various example features extracted from data received from a sensor of an example sensor assembly, such as the sensor assembly 202 or 203, or the sensor assemblies shown in FIGS. 12A-18C. For example, FIG. 9A illustrates example mean absolute values of EMG signals. FIG. 9B illustrates example mean absolute values of MMG signals captured with a Hall Effect sensor in response to magnet movement. FIG. 9C illustrates example mean absolute values of accelerometer readings. FIG. 9D illustrates example peak values from gyroscope readings. Such features and other data can be communicated to a pattern recognition classifier to determine movement data. For example, the movement data can provide an indication or classification of an intended movement. This movement classification can be decoded into motor control signals to drive the prosthetic hand and wrist (e.g., thumb rotation, wrist rotation, hand flexion/extension, etc.).

In some embodiments, the prosthetic system can include one or more grommets for attaching one or more of the sensor assemblies described herein to a POD or a component thereof, such as a sleeve. For example, as described herein, a grommet can be secured to the POD and a sensor assembly can be removably inserted into the grommet. In this way, the sensor assembly can be positioned in a predetermined or fixed location, relative to the POD or the user's limb. A prosthetic system can include a grommet for each sensor assembly.

Figure 10A:
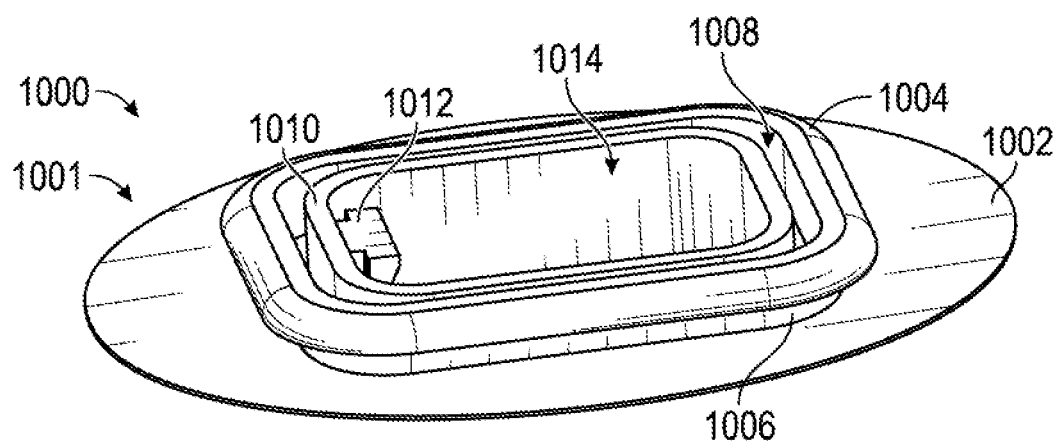
FIGS. 10A-10C illustrate a top perspective view, a bottom perspective view, and a side view respectively of an embodiment of a grommet for a sensor assembly.
Figure 10B:
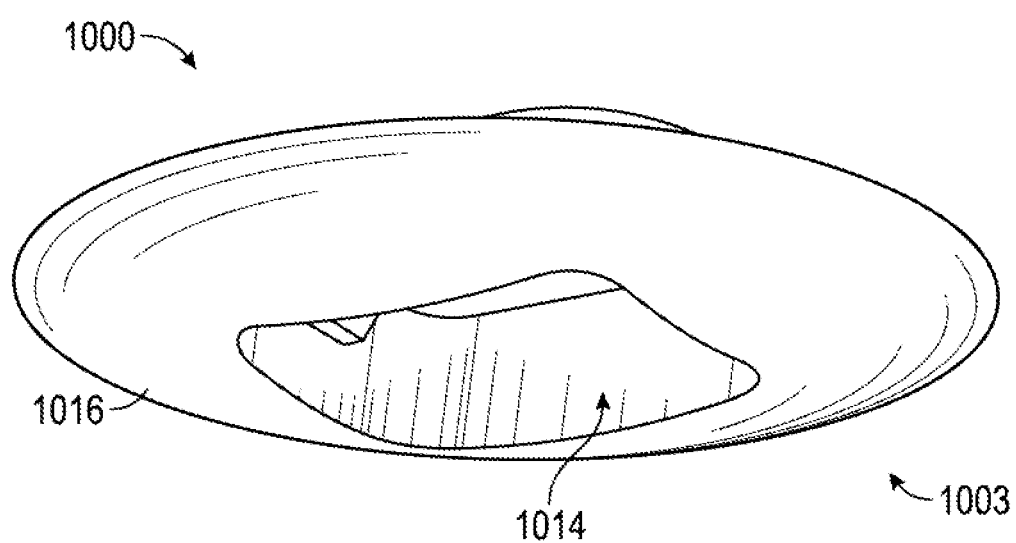
Figure 10C:
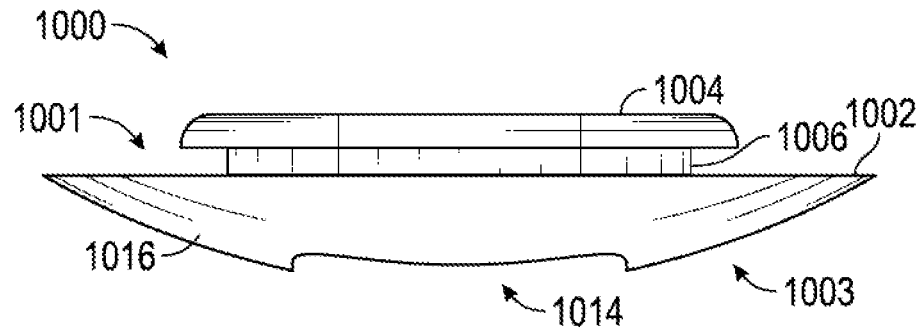

FIGS. 10A-10C illustrate respectively a top perspective view, a bottom perspective view, and a side view of an embodiment of a grommet 1000. The grommet 1000 is configured to attach to a POD or component thereof, such as the lower arm prosthetic system 100 of FIG. 1A or 1B, or a fitting that attaches to a POD, such as the fitting 200 of FIGS. 2A-2B. The grommet 1000 may be formed of plastics, metals, composites, polymers, other suitable materials, or combinations thereof.

The grommet 1000 is configured to removably receive any embodiment of a sensor assembly described herein, such as the sensor assembly 202 of FIGS. 3A-3B, or the sensor assembly 203 of FIGS. 4A-4C, or the sensor assemblies of FIGS. 12A-18C. The grommet 1000 may define an opening 1014, and the grommet 1000 can be configured to receive a sensor assembly at least partially through the opening 1014. The size of the opening 1014 can vary across embodiments. In some cases, the opening 1014 can be sized to fit the sensor assembly. For example, a shape or size of the opening 1014 can match a shape or size of the sensor assembly. In some cases, the opening 1014 can be larger than the sensor assembly. In some cases, the size of the opening 1014 varies across the length or width of the grommet 1000. For example, the opening 1014 may be larger on the upper portion 1001 of the grommet 1000 and smaller at the lower portion 1003 of the grommet 1000. In some cases, such a configuration allows the sensor assembly to be wedged or snuggly fit into the opening 1014 by inserting the sensor assembly into the opening 1014 from the side of the grommet 1000 that corresponds to the upper portion 1001. In some cases, the grommet 1000 may be configured to receive the sensor assembly 202 or 203 when the sensor assembly is without the pair of end portions 362.

The grommet 1000 includes an upper portion 1001, which forms a portion of an outer structure of the grommet 1000. The upper portion 1001 includes a rim 1004 at least partially surrounding an entrance to the opening 1014. The rim 1004 can be curved. The shape of the rim 1004 can vary across embodiments. In some cases, the shape of the rim 1004 matches a shape the entrance of the opening 1014. The rim 1004 can extend away from an upper surface 1004 of the grommet via an extension portion 1006. The upper surface 1004 of the grommet can extend radially about the rim 1004. The upper surface 1004 can be relatively flat.

The grommet 1000 includes an internal socket 1010 configured to receive a sensor assembly. The internal socket 1010 can include an attachment portion 1012 for facilitating securement of the sensor assembly to the grommet 1000. The attachment portion 1012 can be a t-shaped attachment portion. The attachment portion 1012 can extend from or be connected to an internal side of the internal socket 1010. The internal socket 1010 can be positioned such that it is at least partially surrounded by the rim 1004. In some cases, the grommet 1000 can include a groove 1008 between the internal socket 1010 and the rim 1004 or the extension portion 1006.

The grommet 1000 includes a lower portion 1003, which forms a portion of an outer structure of the grommet 1000. The lower portion 1003 includes a lower surface 1016. The lower surface 1016 can be relatively flat or convex. The lower surface 1016 can define an entrance to the opening 1014, described above.

Figure 11:
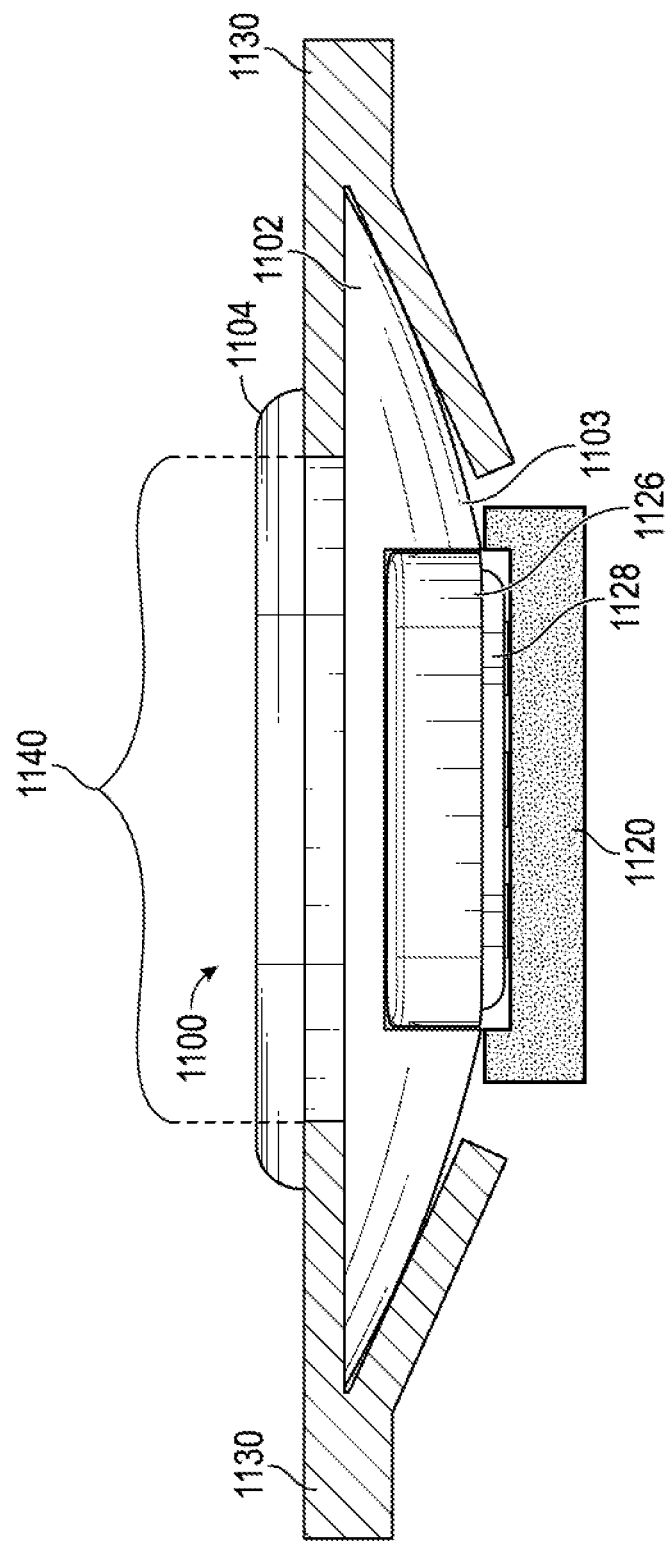
FIG. 11 illustrates a partial cross sectional side view of an example sensor assembly removably inserted into an example grommet and the grommet attached to a socket of a POD.

FIG. 11 illustrates a cross sectional representation of a side view of an example sensor assembly 1126 removably inserted into an example grommet 1100 and the grommet 1100 attached to a socket 1130 of a POD. The sensor assembly 1126 can be an embodiment of the sensor assembly 202 of FIGS. 3A-3B or sensor assembly 203 of FIGS. 4A-4C. The grommet 1100 can be an embodiment of the sensor assembly grommet 1000 of FIGS. 10A-10C.

As shown, the sensor assembly 1126 is positioned within the grommet 1100 such that a support 1128 of the sensor assembly 1106 is substantially flush with a lower portion 1103 of the grommet 1100 and is positioned to contact a user of the POD (e.g., contact the user's skin 1120). Furthermore, the grommet 1100 is positioned within a socket 1104 of a POD. For example, the socket 1104 can define an aperture 1140 through which the grommet 1100 can be inserted or attached. When attached through the aperture 1140 of the socket 1104, the grommet 1100 can coupled to the socket 1104 by sandwiching a portion of the socket 1130 between the rim 1104 of the grommet and an upper surface 1102 of the grommet such that the grommet 1100 is secured to the POD. The support 1128 may be biased toward the user's skin by the springs, as described herein, to ensure contact with the user's limb. The support 1128 may move distally or away from the user in response to muscle movements, thus causing the support 1128 and any sensors attached thereto, such as EMG pickups, accelerometers, Hall Effect sensors, magnets, other distance-detection components, etc. as described herein, to correspondingly move in that direction as well.

Figure 12A:
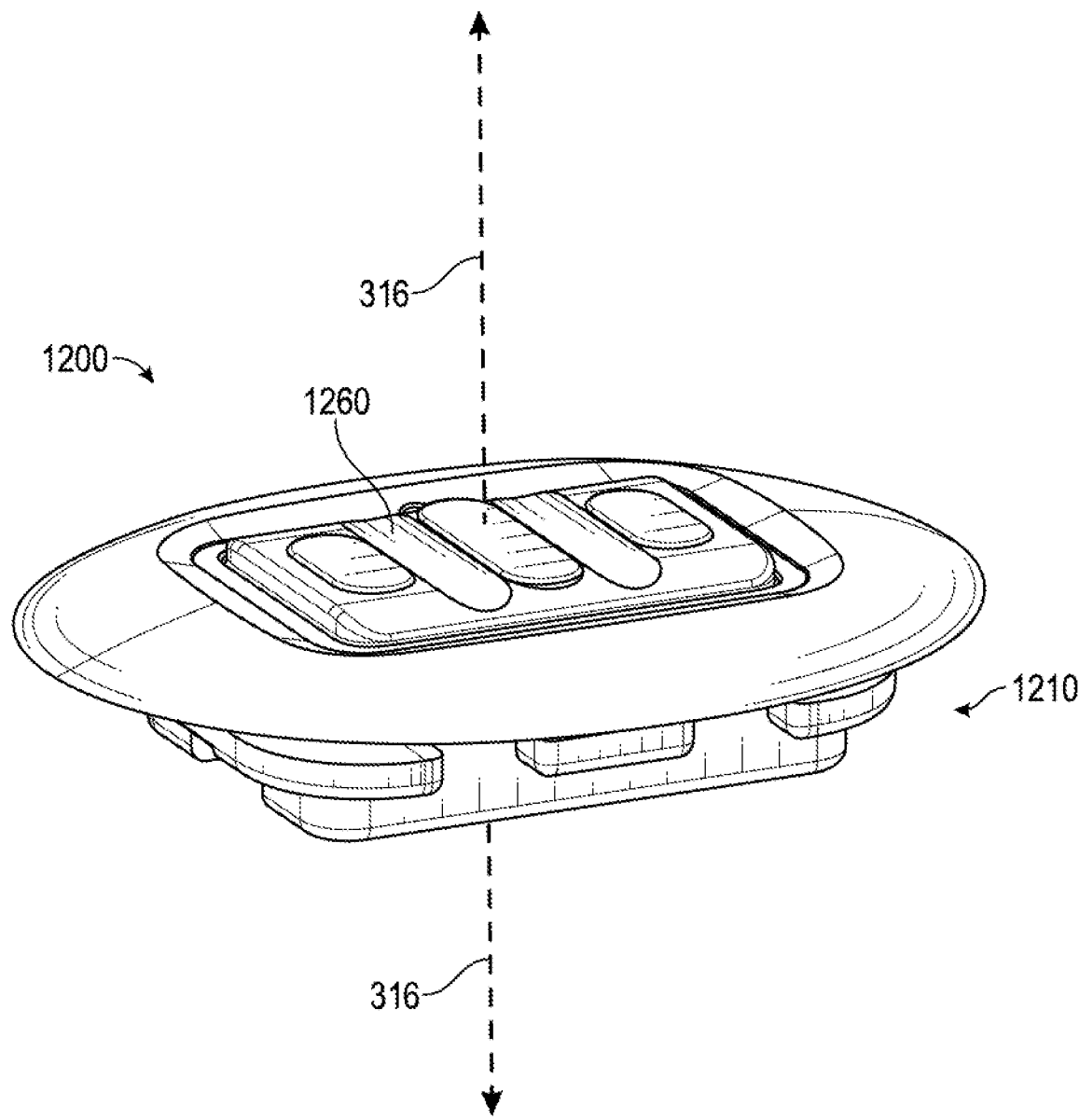
FIG. 12A illustrates a perspective view of another embodiment of a sensor assembly removably inserted into another embodiment of a grommet.
Figure 12B:
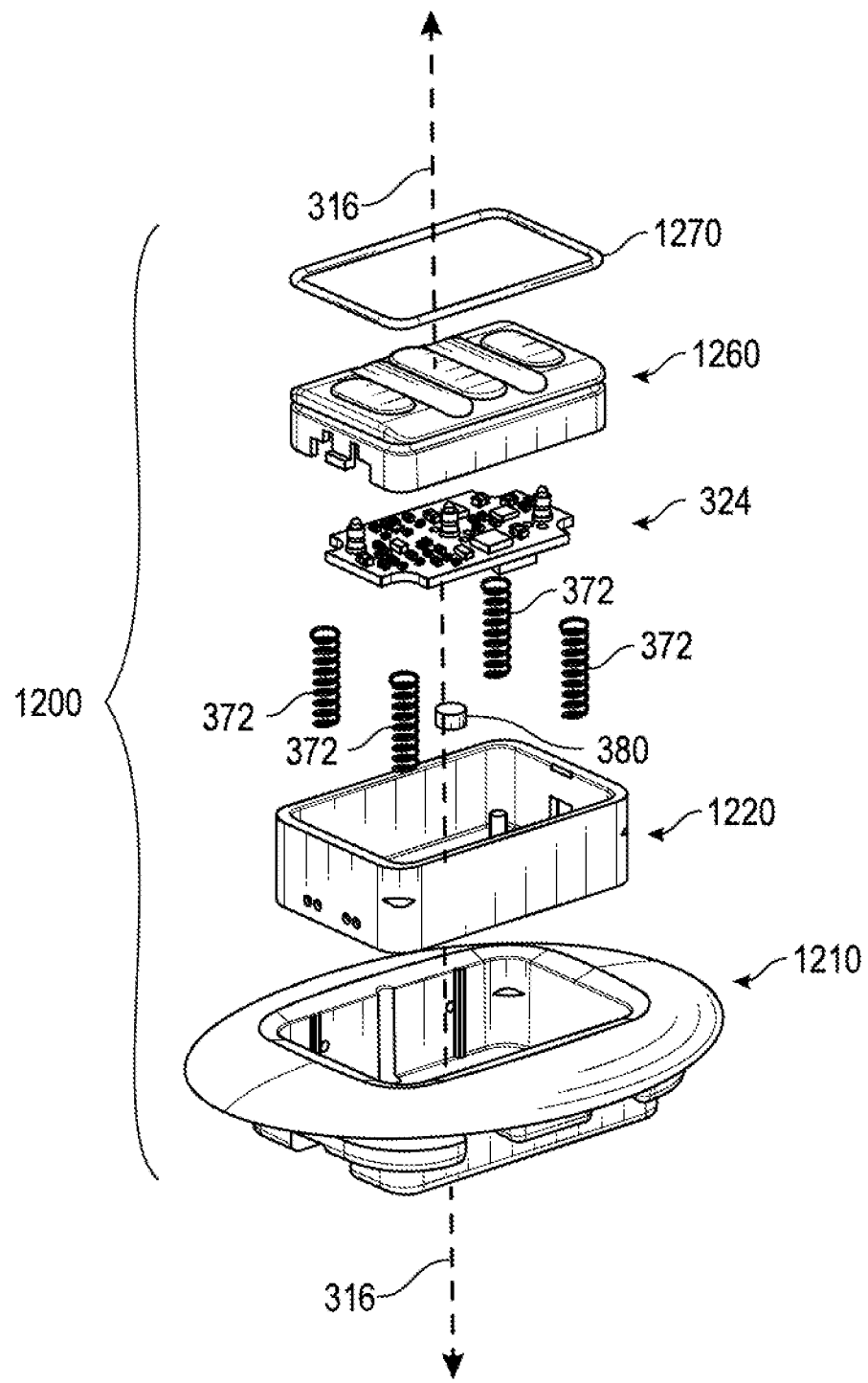
FIG. 12B illustrates an exploded view of the sensor assembly and grommet of FIG. 12A.
Figure 13A:
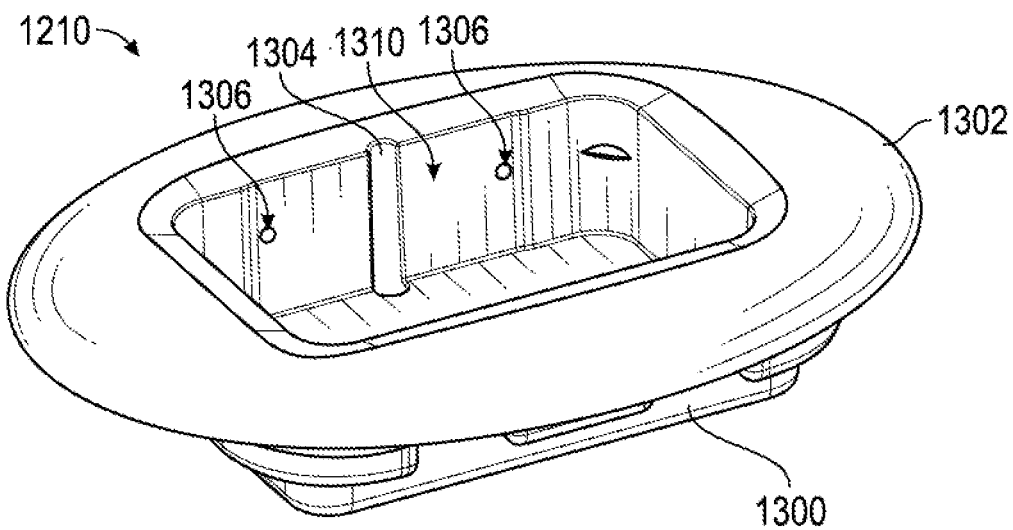
FIGS. 13A-13D illustrate various views of the grommet of FIGS. 12A and 12B.
Figure 13B:
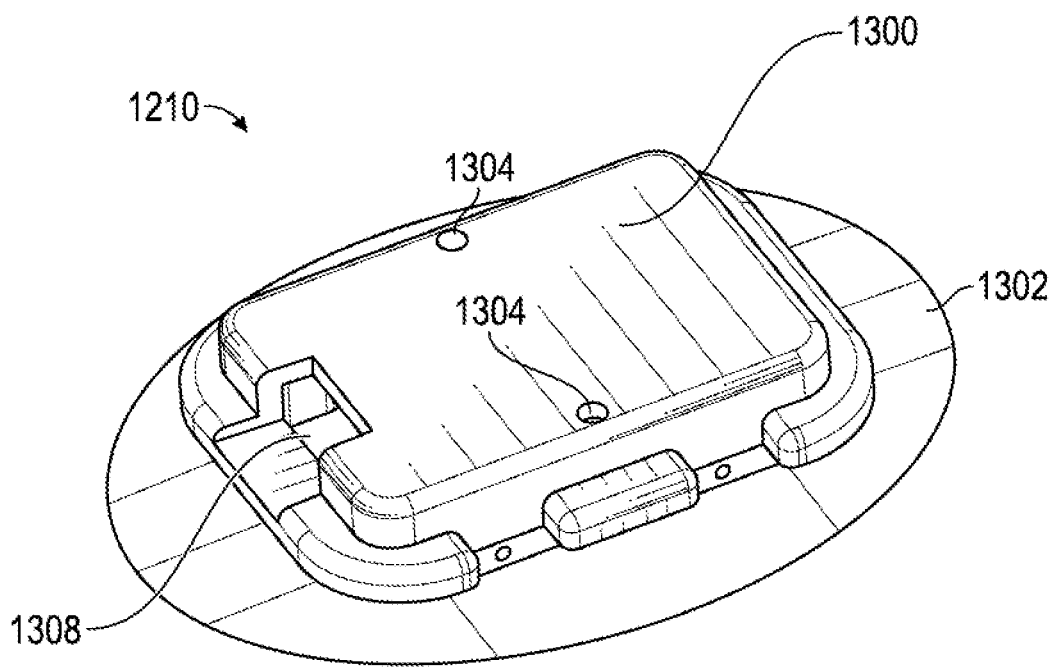
Figure 13C:
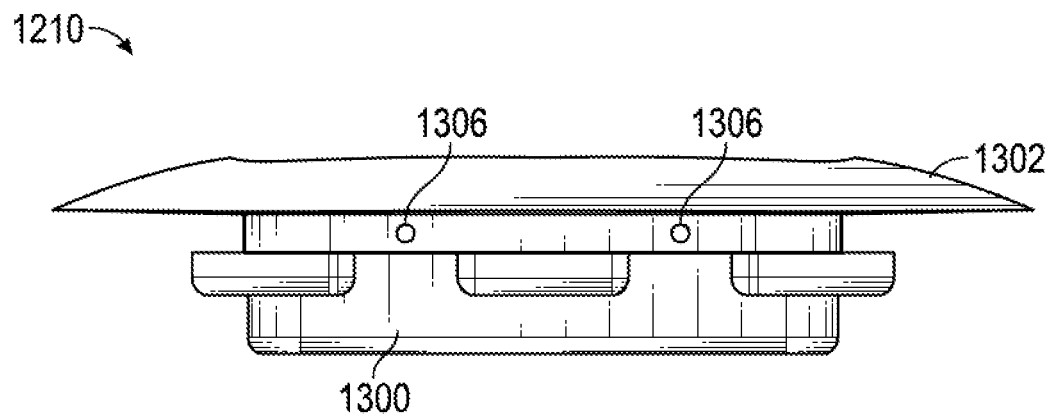
Figure 13D:
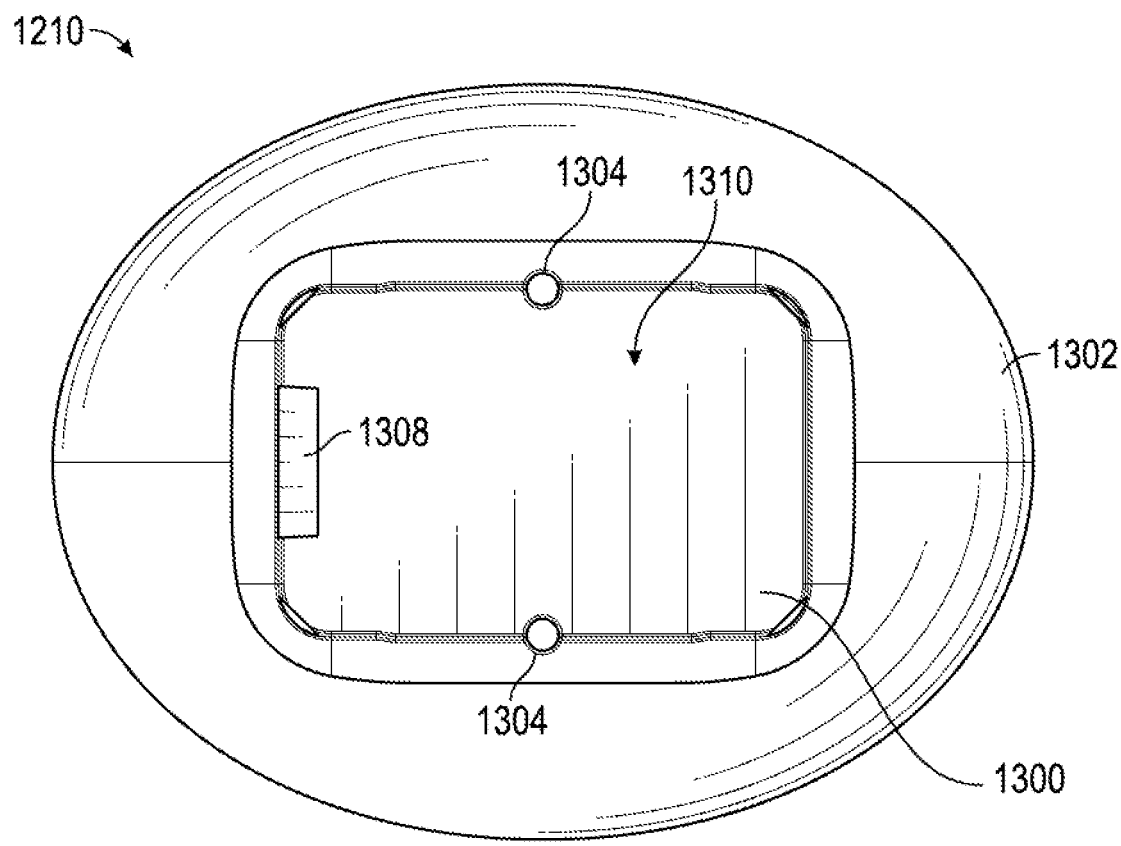

With reference to FIGS. 12A and 12B, another example embodiment of a sensor assembly 1200 is disclosed. The sensor assembly 1200 may include any of the features or functions of any other sensor assembly described herein, and vice versa, except as otherwise described. The sensor assembly 1200 may include a grommet 1210, a housing 1220, a magnet 380, springs 372, the circuit board 324, a support 1260, and/or an O-ring 1270. The grommet 1210 may removably receive the housing 1220, which can include the magnet 380, the springs 372, and the circuit board 324. In some embodiment, the circuit board 324 is mounted to the support 1260 and removably inserted into the housing 1220. The support 1260 may receive the O-ring 1270 and be removably coupled to the housing 1220. The support 1260 may define the central axis 316, which may intersect the support 1260. The axis 316 may be perpendicular to a plane defined by an upper surface of the support 1260. The support 1260 may translate along the central axis 316 in response to forces applied by a user's limb. The housing 1220 and support 1260 may include any of the features or functions of any other housing and support, respectively, described herein, such as the housing 302 and support 304, respectively, and vice versa. For example, the support 1260 may be an overmold, have sidewalls connected to an end wall or upper surface, etc. as further described. Further, the support 1260 may include any of the sensors described herein, and the movement of the support 1260 in response to user muscle movement may generate the various sensor outputs described herein for control of the prosthetic.

FIGS. 13A-13D illustrate various views of the grommet 1210. The grommet 1210 may include any of the features or functions of any other grommet described herein, such as the grommet 1000, and vice versa, except as otherwise described. The grommet 1210 may include a bottom portion 1300 and a top portion 1302. The bottom portion 1300 may be rectangular in shape. The top portion 1302 may be oval or circular in shape. The bottom portion 1300 may include apertures 1306 that are formed on a sidewall (or sidewalls) of the bottom portion 1300. Additionally, the bottom portion 1300 may include an opening 1308 formed on a sidewall of the bottom portion 1300. The opening 1308 may allow wires from the circuit board 324 to extend through. Additionally, the bottom portion 1300 may include openings 1304 formed through a bottom surface of the bottom portion 1300 and partially through the adjacent sidewall. The openings 1304, 1306 may, for example, let air flow through when the housing 1220 is inserted into an opening 1310 of the bottom portion 1300.

The cavity or opening 1310 of the bottom portion 1300 may have a shape that corresponds to a shape of the housing 1220. In the illustrated embodiment, the opening 1310 and the housing 1220 are both rectangular in shape. The bottom portion 1300 may comprise a bottom surface and sidewalls extending upwardly therefrom. The upper portion 1302 may include a flange that extends radially outwardly away from the central axis and have a lower surface configured for contacting an outer surface of a fitting worn by the user. The outer edges of the upper portion 1302 may be located farther outward from the central axis than one or more of the sidewalls of the bottom portion 1300. The planform of the flange (as viewed from the top/bottom, e.g., see FIG. 13D) may be rounded, e.g. elliptical or oval as shown, or other shapes, such as circular, square, rectangular, etc. The bottom portion 1300 may have other shapes, such as square, segmented, polygonal, rounded, oval, circular, etc.

Figure 14B:
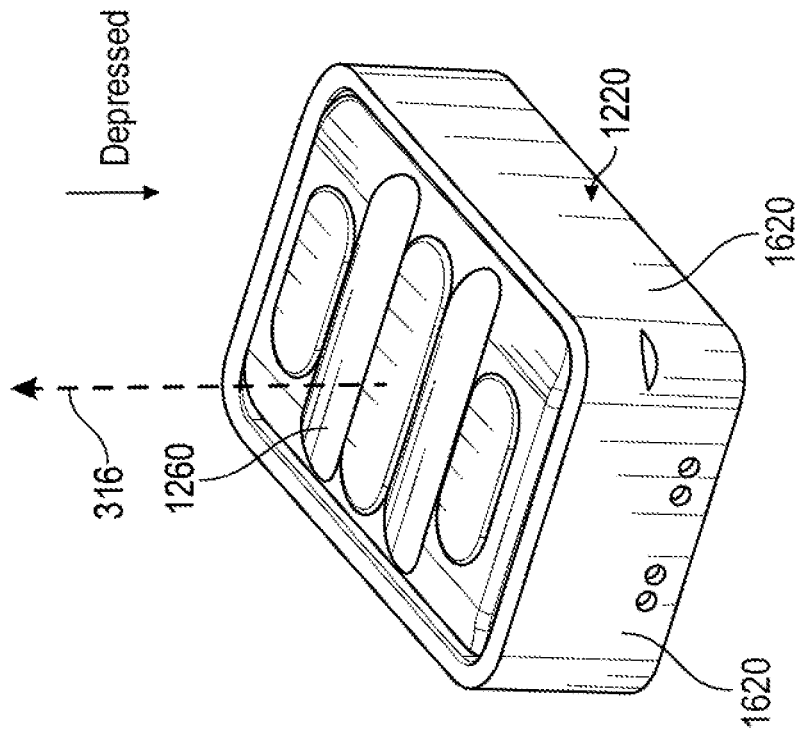
FIGS. 14A and 14B illustrate perspective views of the example sensor assembly of FIGS. 12A and 12B with a support located in different positions.
Figure 14A:
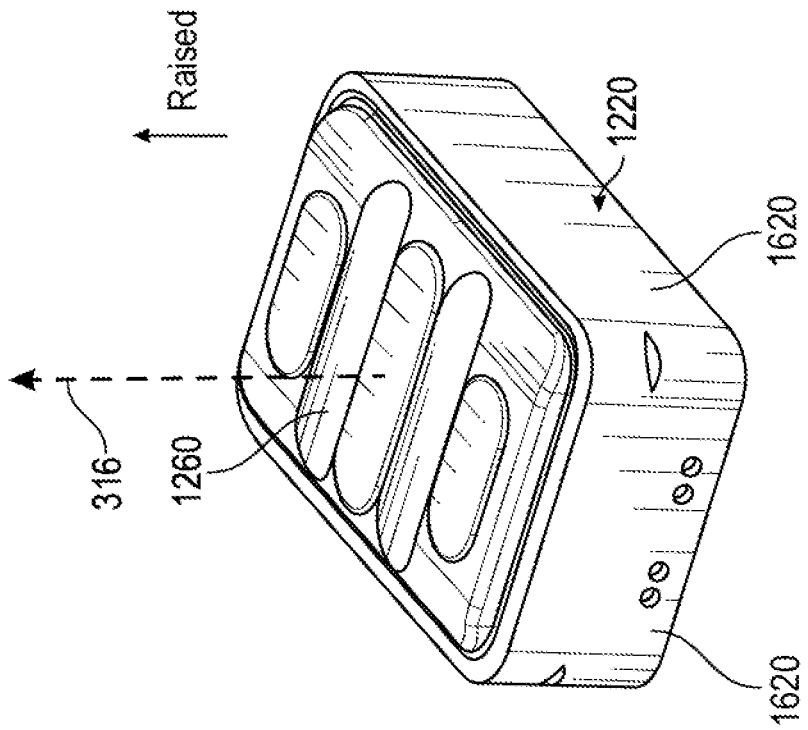

FIGS. 14A and 14B illustrate the housing 1220 and support 1260, and internal electronics and components, assembled together and without the grommet 1210. In some embodiments, the sensor assembly may include the housing 1220, support 1260, and internal electronics/components and not include the grommet. FIGS. 14A and 14B show different axial positions of the support 1260 along the central axis 316 with respect to the housing 1220. In FIG. 14A, the support 1260 is in a first position (that is, a raised position relative to the housing 1220) and in FIG. 14B, the support 1260 is in a second position (that is, a lowered or depressed position relative to the housing 1220). In some embodiments, a proximal-most portion of the support 1260 may protrude beyond a proximal-most portion of the housing 1220 in the raised position, so that the support 1260 is exposed beyond the housing 1220. In some embodiments, the support 1260 may not protrude proximally beyond the housing 1220 in the raised position.

The springs 372 may be positioned between the housing 1220 and the support 1260 to allow the support 1260 to move between the first position and the second position. In some embodiments, the springs 372 may bias the support 1260 to the first position (that is, the raised position). For example, the support 1260 may move to the second, lowered position when an external force is applied (for example, towards the housing 1220) and may move towards the first, raised position when the external force is removed. When the external force is applied, the springs 372 positioned between the support 1260 and the housing 1220 may be compressed and store elastic potential energy. When the external force is removed, the stored elastic potential energy of the springs 372 may be released and converted into a kinetic energy, pushing (or urging) the support 1260 towards the first position (that is, the raised position). The support 1260 may uniformly depress as shown in FIG. 14B, for instance where each spring is compressed a similar or same amount. In some embodiments, the support 1260 may depress different amounts at different locations of the support 1260, for instance where one or more of the springs compresses less or more than one or more of the other springs. The support 1260 may therefore by angled when depressed. Further, depending on the user, fitting and alignment when assembled, the support 1260 may or may not be uniform or level in the raised, first position shown in FIG. 14A. For instance, the support 1260 may be partially depressed in the first, raised position shown in FIG. 14A, and then depress further when acted on by a user's muscle to take a second, even more depressed position shown in FIG. 14B. Thus, any movement between the raised and depressed position may be relative to the other, previous position.

Figure 15A:
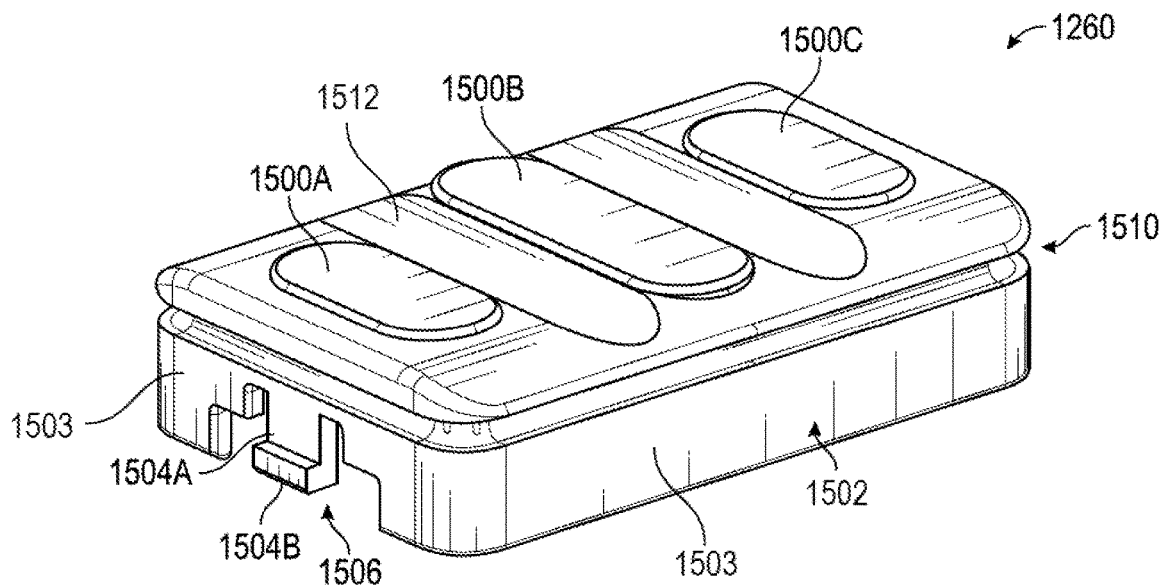
FIG. 15A illustrates a perspective view of the support of FIGS. 12A and 12B.
Figure 15B:
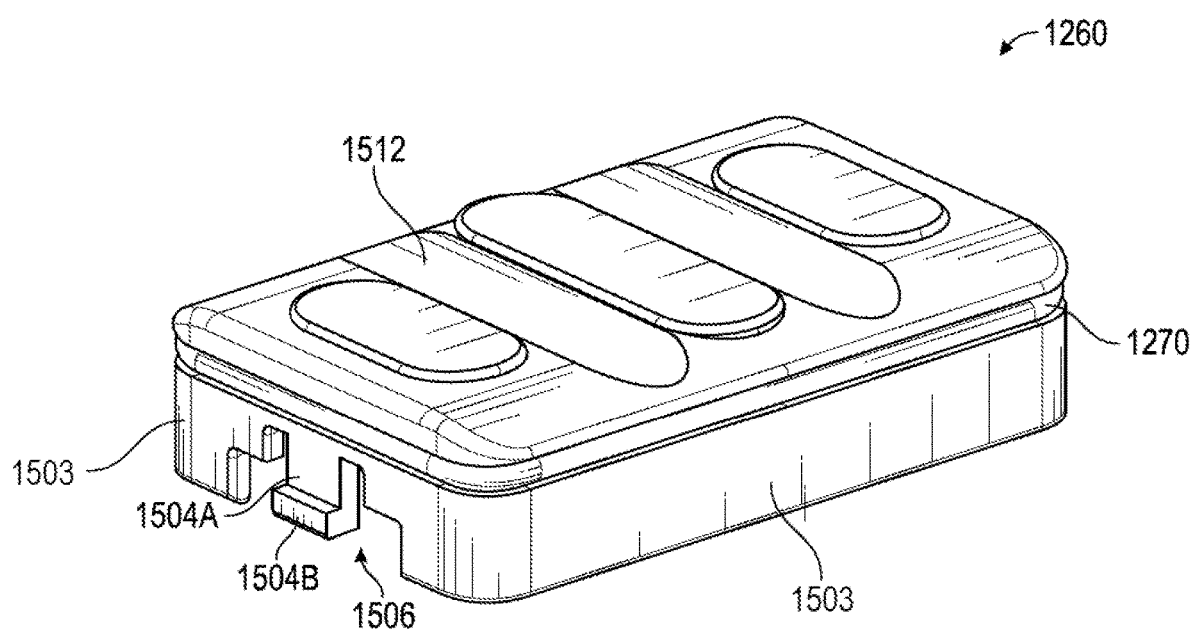
FIG. 15B illustrates a perspective view of the support of FIG. 15A with an O-ring.

FIGS. 15A and 15B show the support 1260 in isolation. The support 1260 may include a body 1502 having sidewalls 1503 connected to an upper surface 1512. The body 1502 may include one or more electrode surfaces 1500A, 1500B, 1500C. The positions of the electrode surfaces 1500A, 1500B, 1500C may correspond to positions of pins 1804 (see FIG. 18C). The electrode surfaces 1500A, 1500B, 1500C may be formed on the upper surface 1512 of the body 1502.

The body 1502 may include one or more locking devices 1506. There may be two locking devices 1506 located at opposite longitudinal ends of the body 1502 as shown (only one is visible in the figure as oriented). The locking device 1506 may include a first portion 1504A, such as a tab, extending downward from a side edge of the upper surface 1512 of the body 1502. The locking device 1506 may include a second portion 1504B (for example, a detent or flange) extending outward (for example, away from the body 1502) from a distal end of the first portion 1504A. The first portion 1504A may flex to allow the second portion 1504B to engage with an opening or recess in the housing 1220. The body 1502 may include a groove 1510 that may receive the O-ring 1270. The groove 1510 may be an inward recess of the body 1502 extending around the perimeter of the sidewalls 1503. The groove 1510 may be located in the sidewalls 1503 near the upper surface 1512. It is understood that the use of "upper," "lower," and the like is for sake of description only, and does not limit the scope of the disclosure. For example, when the sensor assembly is used, the "upper" surface 1512 may be facing upward, downward, or to the side, depending on the location of the sensor assembly on the user and fitting.

Figure 16A:
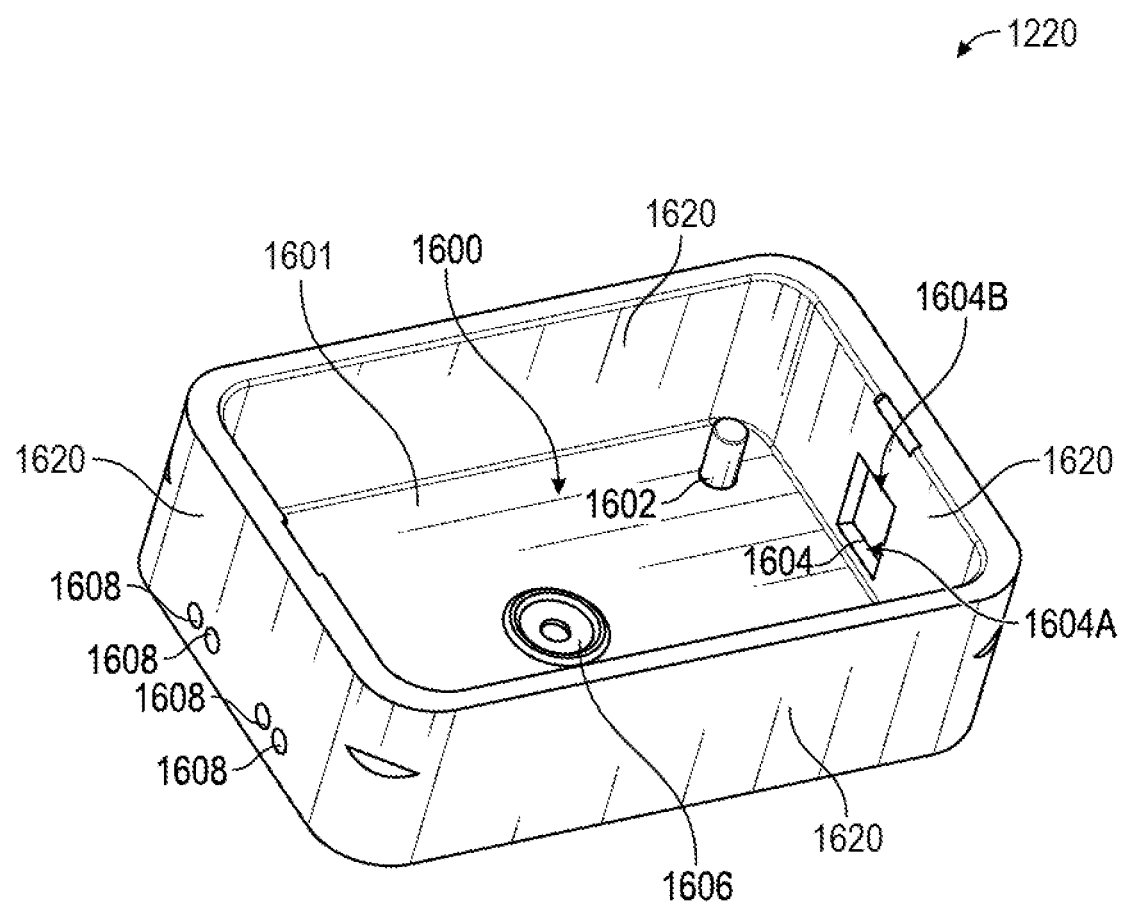
FIG. 16A illustrates a perspective view of an electrode base of the sensor assembly of FIGS. 12A and 12B.
Figure 16B:
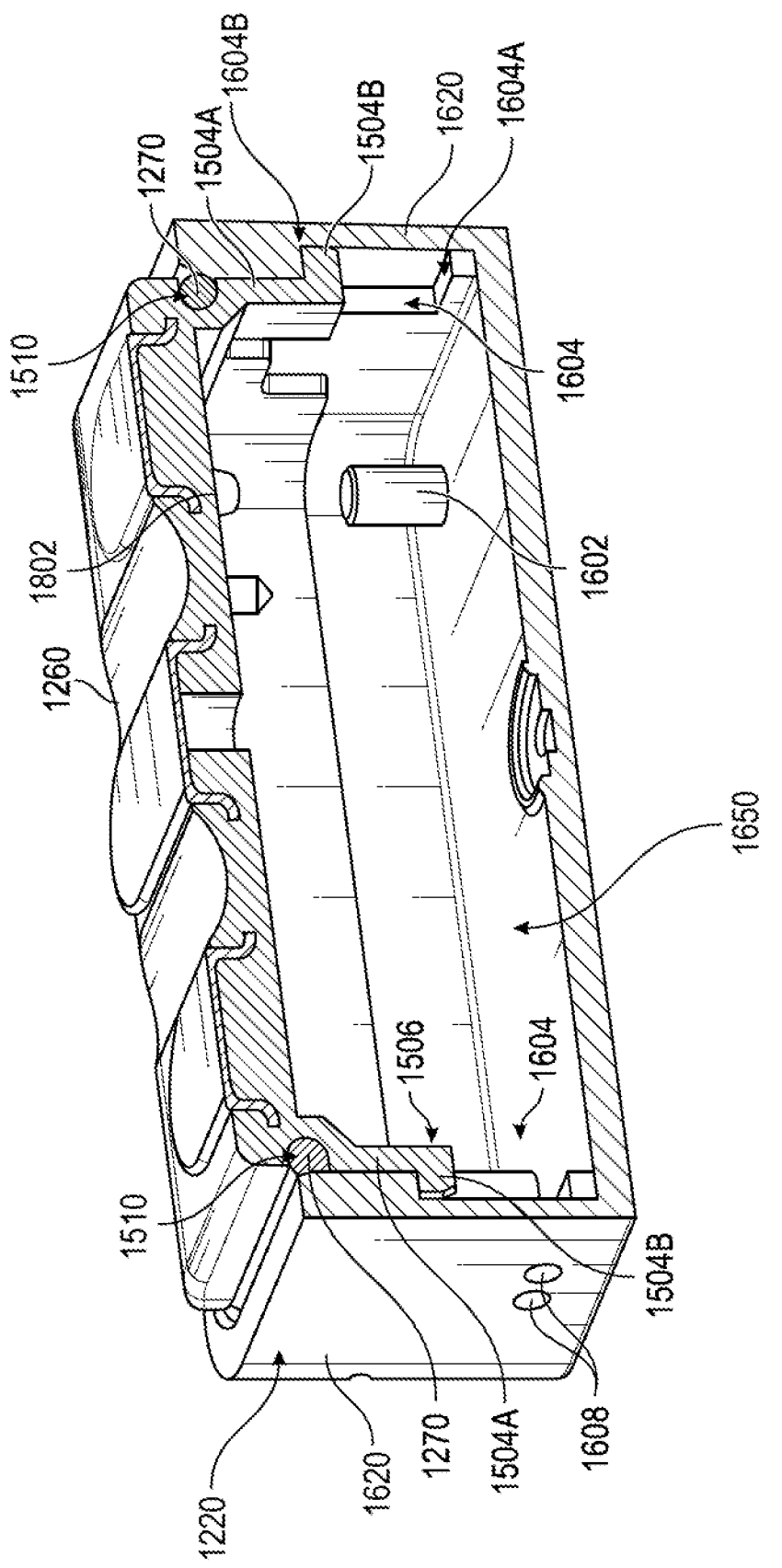
FIG. 16B illustrates a cross-sectional, perspective view of the electrode base of FIG. 16A removably coupled with the support of FIG. 15B.

FIGS. 16A and 16B show top perspective and cross-section perspective views, respectively, of the housing 1220 in isolation. The housing 1220 may include a cavity 1600, protrusions 1602, cutouts 1604, a slot 1606, and/or openings 1608. The cavity 1600 may be formed by one or more sidewalls 1620 of the housing 1220 and may be dimensioned and shaped to slidingly receive the body 1502 (see FIG. 15A) of the support 1260. The sidewalls 1620 may extend away from a floor 1601. As shown in the illustrated embodiment, the cavity 1600 may be substantially rectangular in shape. In some embodiments, the cavity 1600, and/or the floor 1601 and sidewalls 1620, may have any of the shapes or configurations described herein with respect to the support 1260, such as square, rounded, segmented, etc. The protrusions 1602 may be upwardly extending columns or poles that receive the springs 372 slidingly over the protrusions 1602. In the illustrated embodiment, the protrusions 1602 may be positioned at the corners of the housing 1220 such that the springs 372 are positioned at the corners of the housing 1220 (see FIG. 18C). There may be four protrusions 1602 and springs 372 as shown, or there may be one, two, three, five, six, seven, eight or more of the protrusions 1602 and springs 372.

The cutouts 1604 may be formed on an inner surface of the one or more of the sidewalls 1620 of the housing 1220 that form the cavity 1600. The cutouts 1604 may extend completely through the sidewall 1620 such that it forms an opening through the sidewall 1620. The cutout 1604 may extend only partially into the sidewall 1620 such that it forms a recess in the inner surface of the sidewall (see, e.g., FIG. 16B). The cutouts 1604 may receive the second portion 1504B of the locking device 1506 of the support 1260. The cutouts 1604 may include a top edge 1604B and a bottom edge 1604A, which together can limit vertical movement of the second portion 1504B of the locking device 1506. For example, the second portion 1504B may be positioned between the top edge 1604B and the bottom edge 1604A. The top edge 1604B may contact an upper surface of the second portion 1504B to limit movement of the support 1260 away from the housing 1220, for example in the raised position. The bottom edge 1604A may contact a lower surface of the second portion 1504B to limit movement of the support 1260 toward the housing 1220, for example in the depressed position.

The openings 1608 may allow wires from the circuit board 324 to extend through and out of the housing 1220. The slot 1606 may receive and secure a component such as a magnet, for example the magnet 380 shown in FIG. 3B. The magnet 380 may be removably inserted into the slot 1606.

As shown in FIG. 16B, the O-ring 1270 may be positioned between the groove 1510 of the support 1260 and the inner surface of the sidewalls of the housing 1220. The contact between the O-ring 1270 and the groove 1510, and the contact between the O-ring 1270 and the inner surface of the sidewalls 1620 of the housing 1220 may create a seal between the housing 1220 and the support 1260 to prevent unwanted substances (for example, water or dust) from traversing the space between the housing 1220 and the support 1260 and entering the enclosure 1650 formed by the housing 1220 and support 1260 to prevent contamination of the electronics therein. The O-ring 1270 may be any type of sealing material, such as rubber, plastic, etc. The O-ring 1270 may have a circular shaped cross-section as shown, or any other shape, such as elongated, planar, etc. The O-ring 1270 may be located axially such that it provides a seal with the housing 1220 and support 1260 in any of the relative raised or depressed positions. The O-ring 1270 may therefore slide along the inner surface of the sidewalls 1620 of the housing 1220 as the support 1260 moves. There may be a single O-ring 1270 as shown, or there may be two, three, four or more O-rings 1270 located vertically separated from each other or adjacent each other.

The second portions 1504B of the locking device 1506 may extend into the cutouts 1604. As the support 1260 moves up and down along the central axis within the cavity 1600 of the housing 1220, the cutouts 1604 may facilitate and limit the movements (for example, upwards and downwards) of the second portions 1504B. The dimensions of the cutouts 1604 (for example, heights of the cutouts 1604) may determine the relative maximum positions of the support 1260 with respect to the housing 1220. For example, when the support 1260 is in the first position (that is, raised position), the second portions 1504B can abut against the top edge 1604B of the cutout 1604 as shown in FIG. 16B. The O-ring 1270 may seal off the lateral spaces between adjacent sidewalls of the housing 1220 and support 1260 in this raised position. When the support 1260 is in the second position (that is, lowered or depressed position), the second portions 1504B can abut against the bottom edge 1604A of the cutout 1604. The bottom edge of the cutout 1604 can prevent further downward movement of the support 1260 with respect to the housing 1220. The O-ring 1270 may seal off the lateral spaces between adjacent sidewalls of the housing 1220 and support 1260 in this depressed position.

Figure 17A:
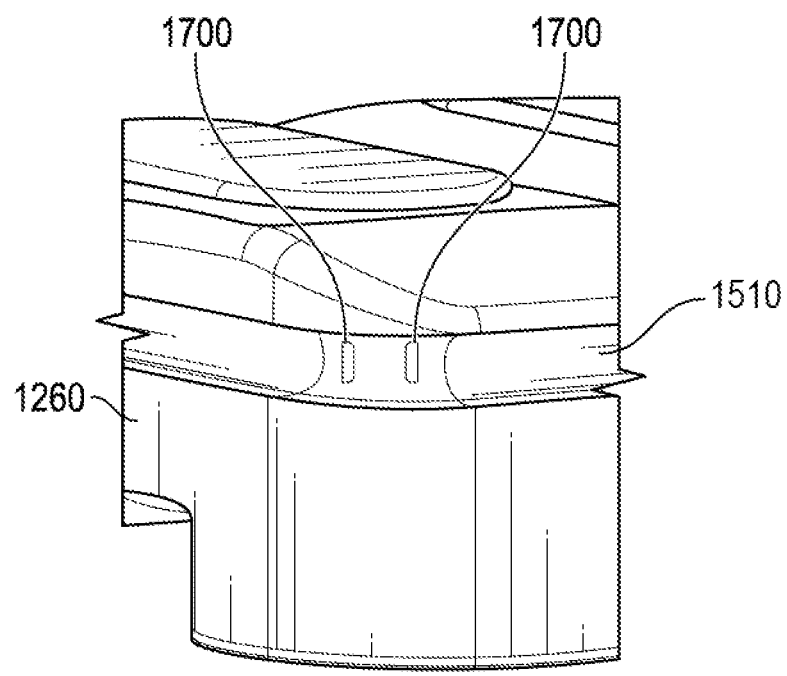
FIG. 17A illustrates a partial perspective view of a groove of the support of FIG. 15A.

FIG. 17A shows a close-up, perspective view of a corner portion of the groove 1510 of the support 1260. Corner portions of the groove 1510 may include one or more ridges 1700 protruding outwardly from within the groove 1510. In the illustrated embodiment shown in FIG. 17A, the groove 1510 may include two ridges 1700 extending axially and spaced apart. There may be three, four, five or more ridges 1700.

Figure 17B:
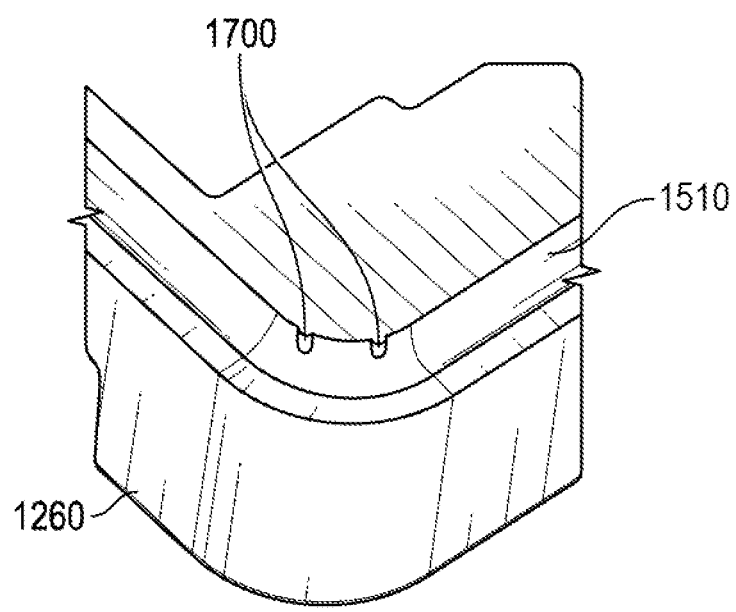
FIG. 17B illustrates a cross-sectional view of the groove of FIG. 17A.
Figure 17C:
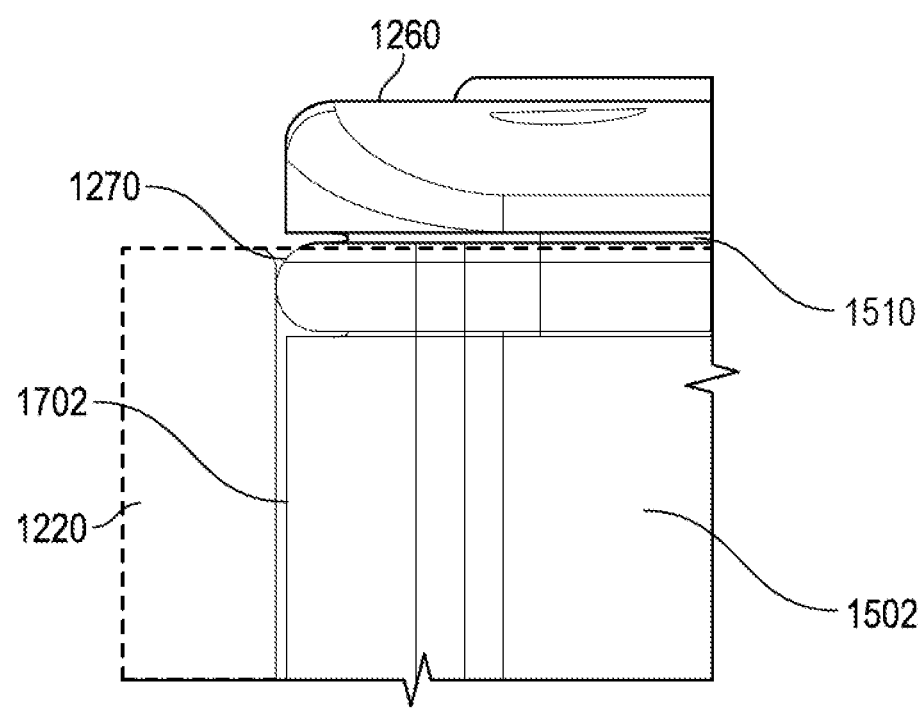
FIG. 17C illustrates a side, close-up view of the support of FIG. 15B with an O-ring.

FIG. 17B illustrates a top, cross-sectional view of a corner portion of the groove 1510, showing cross-sectional shapes of the ridges 1700. As shown in FIG. 17B, the ridge 1700 may have a semi-circular cross-section shape, and/or have rounded edges. The ridge 1700 may be positioned at or about the corners of the groove 1510, and cause the O-ring 1270 to stretch a bit more at the corners. In some embodiments, the ridge 1700 can cause the O-ring 1270 to protrude outwards a bit to tighten the O-ring 1270 and ensure a secure fit around the groove 1510. Contact between the housing 1220 and the O-ring 1270 may, as shown in FIG. 17C, leave a gap 1702 between the housing 1220 and the body 1502 of the support 1260 to reduce friction during movement.

Figure 18A:
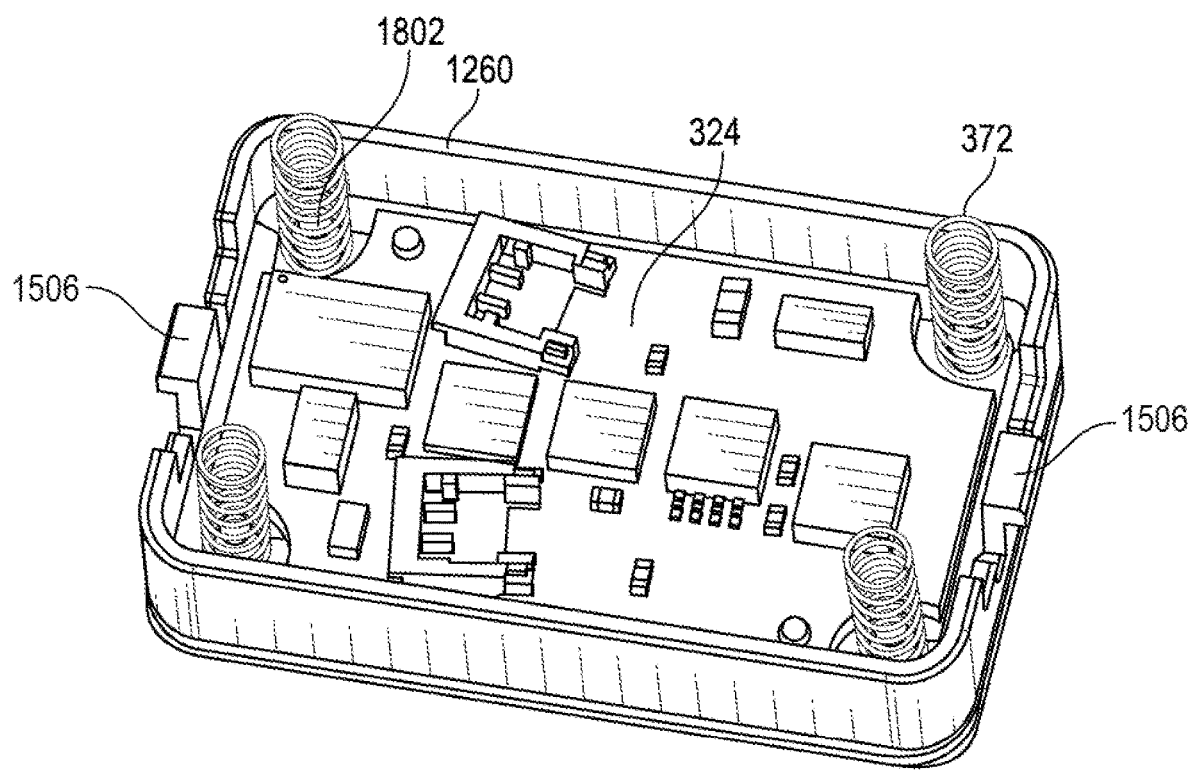
FIG. 18A illustrates a bottom perspective view of the support of FIGS. 15A and 15B with an electrode printed-circuit-board (PCB) and springs.
Figure 18B:
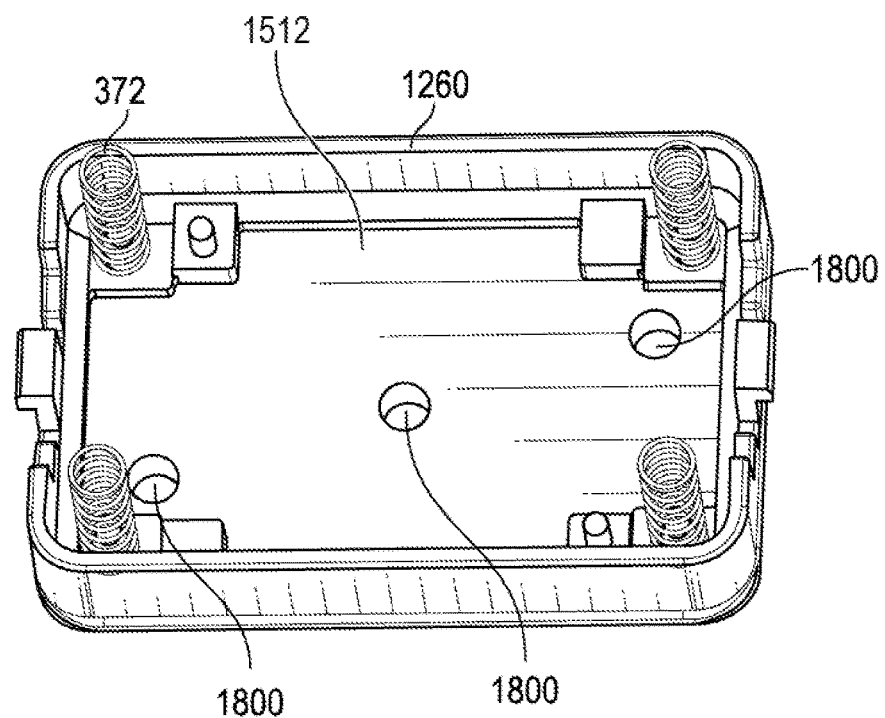
FIG. 18B illustrates a bottom perspective view of the support of FIG. 18A without the electrode PCB.
Figure 18C:
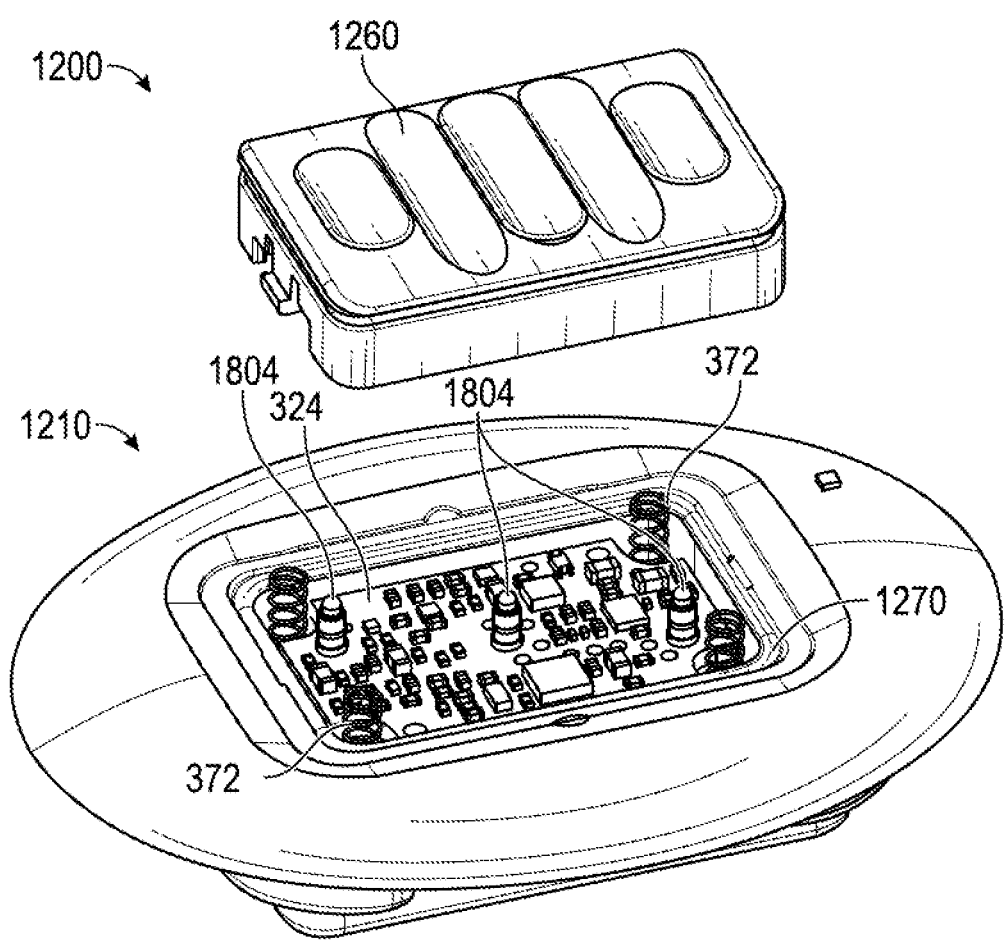
FIG. 18C illustrates a perspective, exploded view showing the sensor assembly and grommet of FIG. 12A with the support separated from the rest of the sensor assembly.

With reference to FIGS. 18A-18C, the support 1260 can receive the circuit board 324 and other electronic components. In some embodiments, the support 1260 may include the electronic components as described herein with respect to the sensor assembly 202. Further, the pins 1804 (see FIG. 18C) positioned on the circuit board 324 may extend through recesses or apertures 1800 in the upper surface 1512 and contact the electrode surfaces 1500A, 1500B, 1500C when assembled. The support 1260 can include protrusions 1802 that are positioned at the corners (see FIG. 16B). The protrusions 1802 may receive the springs 372 and secure them in place during use of the sensor assembly 1200. The protrusions 1802 of the support 1260 and the protrusions 1602 of the housing 1220 may be aligned when assembled. For example, the protrusions 1802 may be positioned above the protrusions 1602 when the support 1260 is placed (or inserted) within the cavity 1600 of the housing 1220. As such, the protrusions 1802 and the protrusions 1602 can together secure opposing ends of the springs 372 in place during use. To assemble the sensor assembly with the electronics and sensors therein, the first portions 1504A of the locking devices 1506 may be flexed inward to slide the support 1260 and housing 1220 together, and the first portions 1504A may then flex outward when located within the cutouts 1604.

Various modifications to the implementations described in this disclosure may be readily apparent to those skilled in the art, and the generic principles defined herein may be applied to other implementations without departing from the spirit or scope of this disclosure. Thus, the disclosure is not intended to be limited to the implementations shown herein, but is to be accorded the widest scope consistent with the claims, the principles and the novel features disclosed herein. The word "example" is used exclusively herein to mean "serving as an example, instance, or illustration." Any implementation described herein as "example" is not necessarily to be construed as preferred or advantageous over other implementations.

Any specific order or hierarchy of steps or blocks in any disclosed process is an example of a sample approach. Based upon design preferences, it is understood that the specific order or hierarchy of steps or blocks in the processes may be rearranged while remaining within the scope of the present disclosure. Any accompanying that claims present elements of the various steps or blocks in a sample order are not meant to be limited to the specific order or hierarchy presented.

A person/one having ordinary skill in the art would appreciate that any of the various illustrative logical blocks, modules, controllers, means, circuits, and algorithm steps or blocks described in connection with the aspects disclosed herein may be implemented as electronic hardware (e.g., a digital implementation, an analog implementation, or a combination of the two, which may be designed using source coding or some other technique), various forms of program or design code incorporating instructions (which may be referred to herein, for convenience, as "software" or a "software module"), or combinations of both.

Certain features that are described in this specification in the context of separate implementations also may be implemented in combination in a single implementation. Conversely, various features that are described in the context of a single implementation also may be implemented in multiple implementations separately or in any suitable sub-combination. Moreover, although features may be described above as acting in certain combinations and even initially claimed as such, one or more features from a claimed combination may in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. In some cases, the actions recited in the claims may be performed in a different order and still achieve desirable results.

In general, terms used herein are generally intended as "open" terms (e.g., the term "including" should be interpreted as "including but not limited to," the term "having" should be interpreted as "having at least," the term "includes" should be interpreted as "includes but is not limited to," etc.). If a specific number of an introduced claim recitation is intended, such an intent will be explicitly recited in the claim, and in the absence of such recitation no such intent is present.

For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

What is claimed is:

1. A sensor assembly for a prosthetic or orthotic device (POD) comprising:
   a housing defining a central axis and configured to be attached with the POD;
   a support moveably connected with the housing such that the support is configured to move relative to the housing along the central axis, the support forming an enclosure with the housing;
   at least one sensor, the at least one sensor comprising a magnetic sensor and an electromyography (EMG) sensor; and
   a circuit board attached with the support and in electrical communication with the at least one sensor.

2. The sensor assembly of claim 1, wherein the EMG sensor comprises multiple EMG pickups carried by the support and configured to contact skin of a user of the POD and to move along with the support.

3. The sensor assembly of claim 1, wherein the magnetic sensor is a Hall Effect sensor, the sensor assembly further comprising a magnet, the magnet configured to generate a magnetic field that is detected by the Hall effect sensor.

4. The sensor assembly of claim 3, wherein the magnet is attached with the housing and the Hall effect sensor is attached with the support and configured to move along with the support.

5. The sensor assembly of claim 1, further comprising at least one biasing member configured to bias the support in a direction away from the housing and toward a user.

6. The sensor assembly of claim 5, wherein the at least one biasing member comprises a compression spring.

7. The sensor assembly of claim 1, further comprising an IMU, the IMU configured to detect a vibromyography (VMG) signal associated with a muscle of a user.

8. The sensor assembly of claim 7, wherein the IMU comprises at least one of an accelerometer, a gyroscope, or a magnetometer.

9. The sensor assembly of claim 1, wherein the housing comprises a cutout, wherein the support comprises a locking device including a detent, and wherein the cutout is configured to receive the detent of the locking device and facilitate movement of the support relative to the housing.

10. The sensor assembly of claim 1, wherein a top portion of the sensor assembly comprises a groove configured to receive an O-ring, wherein the O-ring is configured to abut against sidewalls of the housing and create a seal.

11. The sensor assembly of claim 1, wherein the at least one sensor comprises the magnetic sensor, an IMU, and the EMG sensor.

12. A sensor assembly for a prosthetic or orthotic device (POD) comprising:
    a housing defining a central axis, wherein the housing is configured to be attached with the POD;
    a support moveably connected with the housing such that the support may move relative to the housing along the central axis, the support forming an enclosure with the housing;
    at least one sensor disposed within the enclosure, the at least one sensor configured to detect a magnitude of a magnetic field and electrical signals associated with a residual limb of a user of the POD; and
    a circuit board disposed within the enclosure and in electrical communication with the at least one sensor.

13. The sensor assembly of claim 12, wherein the at least one sensor comprises:
    an inertial measurement unit (IMU) comprising at least one of an accelerometer, a gyroscope, or a magnetometer;
    an electromyography (EMG) sensor comprising multiple EMG pickups carried by the support and configured to contact the residual limb of the user; and
    a magnetic sensor and a magnet, wherein the magnet is configured to generate the magnetic field that is detected by the magnetic sensor.

14. The sensor assembly of any of claims 12, further comprising at least one biasing member configured to bias the support along the central axis in a direction away from the housing and toward the user.

15. An apparatus for restoring mobility to an amputee, the apparatus comprising:
    a prosthetic or orthotic device (POD);
    a fitting configured to attach to the POD and to a residual limb of a user of the POD; and
    a sensor assembly configured to attach with the fitting and configured to contact the residual limb when the fitting is attached to the residual limb, the sensor assembly comprising:
        an enclosure comprising a housing and a support, wherein the support is moveably connected with the housing, and wherein the support comprises a groove configured to receive an O-ring, wherein the O-ring is configured to abut against sidewalls of the housing and create a seal;
        at least one sensor carried within the enclosure, the at least one sensor comprising an electromyography (EMG) sensor and a magnetic sensor; and
        a circuit board in electrical communication with the at least one sensor.

16. The apparatus of claim 15, wherein the support comprises one or more EMG pickups of the EMG sensor.

17. The apparatus of claim 15, wherein the housing comprises a cutout, wherein the support comprises a locking device including a detent, and wherein the cutout is configured to receive the detent of the locking device and facilitate movement of the support relative to the housing.

18. The apparatus of claim 15, further comprising a grommet configured to attach to the fitting, wherein the sensor assembly attaches to the fitting via the grommet.

19. An apparatus for restoring mobility to an amputee, the apparatus comprising:
    a prosthetic or orthotic device (POD);
    a fitting configured to attach to the POD and to a residual limb of a user of the POD; and
    a sensor assembly configured to attach with the fitting and configured to contact the residual limb when the fitting is attached to the residual limb, the sensor assembly comprising:
        an enclosure comprising a housing and a support, wherein the support is moveably connected with the housing;
        at least one sensor carried within the enclosure, the at least one sensor comprising an electromyography (EMG) sensor and a magnetic sensor; and
        a circuit board in electrical communication with the at least one sensor; and
    a grommet configured to attach to the fitting, wherein the sensor assembly attaches to the fitting via the grommet.

20. The apparatus of claim 19, wherein the support comprises one or more EMG pickups of the EMG sensor.

21. The apparatus of claim 19, wherein the housing comprises a cutout, wherein the support comprises a locking device including a detent, and wherein the cutout is configured to receive the detent of the locking device and facilitate movement of the support relative to the housing.

* * * * *